United States Patent
Ran et al.

(10) Patent No.: US 8,986,657 B2
(45) Date of Patent: *Mar. 24, 2015

(54) METHODS AND SYSTEM FOR DETECTING SOLUBLE AMYLOID-β

(75) Inventors: Chongzhao Ran, Winchester, MA (US); Anna Moore, Dracut, MA (US)

(73) Assignee: The General Hospital Corporation, Boston, MA (US)

( * ) Notice: Subject to any disclaimer, the term of this patent is extended or adjusted under 35 U.S.C. 154(b) by 70 days.

This patent is subject to a terminal disclaimer.

(21) Appl. No.: 13/387,963

(22) PCT Filed: Jul. 29, 2010

(86) PCT No.: PCT/US2010/043700
§ 371 (c)(1),
(2), (4) Date: Apr. 5, 2012

(87) PCT Pub. No.: WO2011/014648
PCT Pub. Date: Feb. 3, 2011

(65) Prior Publication Data
US 2012/0183474 A1  Jul. 19, 2012

Related U.S. Application Data

(60) Provisional application No. 61/230,182, filed on Jul. 31, 2009.

(51) Int. Cl.
| | | |
|---|---|---|
| A61B 5/00 | (2006.01) |
| A61B 5/055 | (2006.01) |
| C07F 5/02 | (2006.01) |
| C07D 213/02 | (2006.01) |
| G01N 33/566 | (2006.01) |
| G01N 33/58 | (2006.01) |

(52) U.S. Cl.
CPC .............. *C07F 5/022* (2013.01); *C07D 213/02* (2013.01); *G01N 33/566* (2013.01); *G01N 33/585* (2013.01); *G01N 2333/4709* (2013.01)
USPC .............................. 424/9.6; 424/9.3; 424/9.37

(58) Field of Classification Search
None
See application file for complete search history.

(56) References Cited

U.S. PATENT DOCUMENTS

2007/0060644 A1* 3/2007 Vander Jagt et al. ......... 514/475
2008/0118938 A1  5/2008 Estrada et al.
2009/0004107 A1* 1/2009 Mukherjee et al. .......... 424/1.89

FOREIGN PATENT DOCUMENTS

WO  94-10569  5/1994
WO  2005-092443  10/2005

OTHER PUBLICATIONS

Bratu MG. Synthesis of curcumin derivatives. 2005 Acta Universitatis Cibiniensis Series E: Food Technology 9:11-16.*
Yang et al. Curcumin inhibits formation of amyloid beta oligomers and fibrils, binds plaques, and reduces amyloid in vivo. 2005 J. Biol. Chem. 280: 5892-5901.*
Garcia-Alloza et al. Curcumin labels amyloid pathology in vivo, disrupts existing plaques, and partially restores distorted neurites in an Alzheimer mouse model. 2007 J. Neurochem. 102: 1095-1104.*
Zhang et al. Synthesis and fluorescent properties of difluoroboron dibenzoylmethane polycaprolactone. 2009 Macromolecules 42: 3092-3097. Published online Mar. 26, 2009.*
Lozada et al. Crystal structure of the curcumin derivative, acetic acid 4-[7-(4-acetoxy-3-methoxyphenyl)-3,5-dioxoheptyl]-2-methoxyphenyl ester. 2004 Anal. Sci. 20: x91-x92.*
Massoud et al. Molecular imaging in living subjects: seeing fundamental biological processes in a new light. 2003 Genes Dev. 17: 545-580.*
Nakada et al. Fluorine-19 NMR imaging of glucose metabolism. 1988 Magn. Reson. Med. 6: 307-313.*
International Search Report as mailed on Apr. 22, 2011 for International Application No. PCT/US2010/043700.

* cited by examiner

*Primary Examiner* — Michael G Hartley
*Assistant Examiner* — Jennifer Lamberski
(74) *Attorney, Agent, or Firm* — Quarles & Brady, LLP

(57) ABSTRACT

The present invention provides methods of detecting soluble amyloid β using curcumin-derived near infrared (NIR) imaging probes. Upon interacting with soluble amyloid β, these probes undergo a range of changes, qualifying them as "smart" probes. In addition, the invention provides methods of detecting soluble amyloid β by positron emission tomography (PET), magnetic resonance imaging (MRI) and multimodal imaging based on the curcumin-derived NIR imaging probes and derivatives thereof.

15 Claims, 15 Drawing Sheets

METHODS AND SYSTEM FOR DETECTING SOLUBLE AMYLOID-β

CROSS-REFERENCES TO RELATED APPLICATIONS

This application represents the U.S. national phase entry of PCT International Application No. PCT/US2010/043700 filed Jul. 29, 2010, and claims the benefit of U.S. Provisional Patent Application Ser. No. 61/230,182 filed on Jul. 31, 2009, incorporated by reference herein.

STATEMENT REGARDING FEDERALLY SPONSORED RESEARCH OR DEVELOPMENT

Not Applicable.

FIELD OF THE INVENTION

The invention relates generally to molecular probes for detecting amyloid-β. In particular, the invention is related to various curcumin derivatives useful for detecting soluble amyloid-β.

BACKGROUND OF THE INVENTION

Amyloid beta (Aβ) species have been shown to play a key role in neuropathology of Alzheimer's Disease (AD); however the exact roles that soluble Aβ species and insoluble amyloid plaques play remain controversial. In past decades, much effort has been put into the research dealing with amyloid plaques, and most of the drug developments for AD have been oriented to eliminate plaques or reduce the formation of these plaques by different approaches. Several drugs, such as the aggregating inhibitor tramiprosate, the humanized monoclonal antibody bapineuzumab, and the γ-secretase inhibitor Flurizan, were developed and underwent clinical trials. Unfortunately, these clinical trials, by and large failed to prove the effectiveness of those drugs. These failures may have been due to poorly organized patient recruitments, which may have been due to a lack of accurate diagnoses to distinguish AD-dementia from other dementia, and to the inability to link the Aβ loading with the degree of dementia. This strongly indicates that reliable diagnoses are essential and, further, consideration should be given to drug development based on the presence of amyloid pro-plaque species, particularly soluble Aβ species.

There are currently no available techniques to reliably monitor the soluble Aβ species in vivo. In recent years, researches have demonstrated that positron emission tomography (PET) can be used as an imaging modality to detect AD pathology. Probe PIB is used for the purpose of early clinical diagnosis, but not for early stages of pathology (it is widely believed that the AD pathology stages are not synchronized with the clinically diagnosed stages, and the correlations between the clinical stage and the degree of pathological abnormality is still unclear).

Molecular optical imaging is a promising modality for early AD pathological detection. Multiphoton and near infrared imaging are the most used optical imaging modalities, based on the fluorescent property of the probes. Although multiphoton microscopy could be very useful in animal research, it is invasive and only provides a very small field-of-view. Near Infrared Imaging (NIR) is a very attractive tool for early AD detection because it has an acceptable depth penetration, is non-invasive, and requires inexpensive instrumentation.

Previous studies have suggested that amyloid plaque burden correlates poorly with Alzheimer's disease (AD) severity. Mounting evidences from recent years have pointed towards the toxicity of the soluble monomeric species as the first manifestation of AD. However, detection of these species in vivo presents an unsolved problem. Most of the techniques such as MRI, PET, and optical imaging used for in vivo detection of AD abnormalities have been focused on plaque imaging. Methods that are capable of detecting soluble Aβ species in vivo are urgently needed. It can be appreciated that these methods will be beneficial for early and accurate diagnosis of AD, and in addition will be helpful for AD drug development.

SUMMARY OF THE INVENTION

The present invention is based, in part, on the inventors discovery of a series of curcumin-based compounds that exhibit specific binding to a wide panel of Aβ species including plaques, aggregates, monomeric Aβ40 and Aβ42 peptides, and even the short core fragment (KLVFF) of those peptides. In vitro tests demonstrated that exemplary compounds CRANAD-2, CRANAD-3 and CRANAD-5 (illustrated in FIG. 1) were able to not only detect plaques in tissue and Aβ aggregates in solution, but also to bind to the dimers and monomers, and to sense the fragments of the Aβ peptide. In contrast, thioflavin T showed specificity only to Aβ aggregates, but no significant fluorescence intensity change upon mixing with monmeric Aβ peptide or segments of Aβ peptide. These data were confirmed by reports that thioflavin T was not able to detect soluble Aβ40/42. Accordingly, it can be appreciated that the compounds and methods of the invention are applicable to detecting both insoluble and soluble Aβ species in vitro. The inventors further demonstrated that the present compounds, including derivatives modified for PET or MRI applications, are capable of detecting both insoluble and soluble Aβ species in vivo. Therefore, the present invention provides reagents and methods useful to monitor the full course of AD amyloidosis pathology in a variety of modalities.

In one aspect, the present invention provides a method for detecting soluble amyloid beta in a sample, comprising the steps of (a) contacting a sample comprising soluble amyloid beta with a compound having the formula $Ar^1$-L-$Ar^2$; (b) illuminating the compound bound to the soluble amyloid beta with near infrared light of a wavelength absorbable by the compound; and (c) detecting fluorescence emitted by the compound wherein the fluorescence corresponds to the soluble amyloid beta contained in the sample. L is a divalent linking group comprising an alkenylene having 5 to 15 backbone carbon atoms, wherein at least two of the backbone carbon atoms form part of a carbonyl or secondary alcohol and $Ar^1$ and $Ar^2$ are each independently alkyl amine-substituted aryl or heteroaryl groups; or L is a divalent linking group comprising an alkenylene having 5 to 15 backbone carbon atoms, wherein at least two of the backbone carbon atoms form part of a difluoroboronate ring; and $Ar^1$ and $Ar^2$ are each independently alkyl amine-substituted aryl or heteroaryl groups. The compound binds soluble amyloid beta in the sample.

In one embodiment, the method is carried out in vitro.

In another embodiment, the presence, absence, or level of the compound's fluorescence in the sample is indicative of a disease state.

In another embodiment, the disease state is Alzheimer's disease.

In another embodiment, L is —CH=CH—(CO)—CH=C(OH)—CH=CH— or —H=CH—(CO)—$CH_2$—C(O)—CH=CH—.

In another embodiment, $Ar^1$ and $Ar^2$ are independently selected from

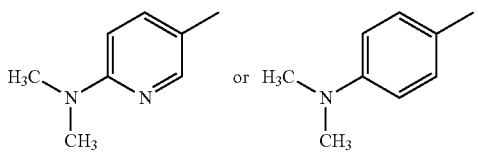

In a preferred embodiment, the compound has the structure:

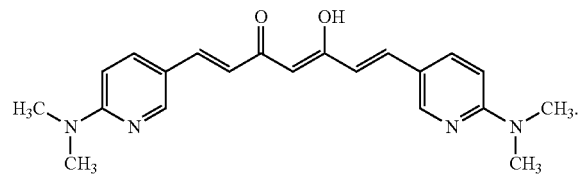 [SMILES: CN(C)c1ccc(/C=C/C(=O)/C=C(O)/C=C/c2ccc(N(C)C)nc2)cn1]

In another embodiment, L is

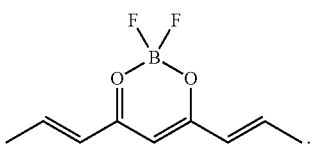

In another embodiment, $Ar^1$ and $Ar^2$ are independently selected from

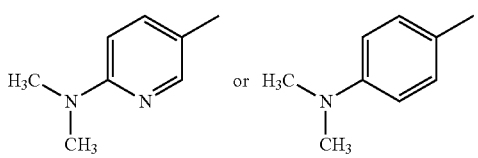

In another preferred embodiment, the compound has the structure:

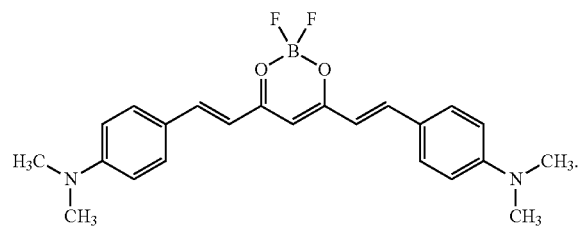

In another embodiment, $Ar^1$ and $Ar^2$ are independently selected from

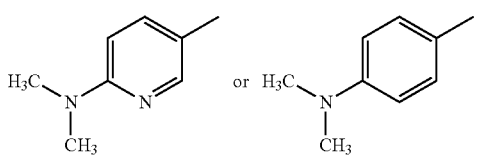

In another embodiment, the compound is capable of binding soluble amyloid beta in both in vitro and in vivo settings.

In another aspect, the present invention provides an in vivo optical imaging method for soluble amyloid beta detection in a subject, comprising (a) administering to a subject a compound having the formula $Ar^1$-L-$Ar^2$; (b) illuminating the compound bound to the soluble amyloid beta with near infrared light of a wavelength absorbable by the compound; and (c) detecting fluorescence emitted by the compound wherein the fluorescence corresponds to the soluble amyloid beta contained in the subject. L is a divalent linking group comprising an alkenylene having 5 to 15 backbone carbon atoms, wherein at least two of the backbone carbon atoms form part of a carbonyl or secondary alcohol and $Ar^1$ and $Ar^2$ are each independently alkyl amine-substituted aryl or heteroaryl groups; or L is a divalent linking group comprising an alkenylene having 5 to 15 backbone carbon atoms, wherein at least two of the backbone carbon atoms form part of a difluoroboronate ring; and $Ar^1$ and $Ar^2$ are each independently alkyl amine-substituted aryl or heteroaryl groups. The compound binds soluble amyloid beta contained in the subject.

In one embodiment, the fluorescence detected in step (c) is used in an additional step to construct an image of the soluble amyloid beta present in the subject.

In another embodiment, step (c) is performed using a light detection or image recording component comprising a charge coupled device (CCD) system or photographic film.

In another embodiment, (b) and (c) are performed using an endoscopic device, a catheter-based device, a diffuse optical tomographic imaging system, phased array technology, confocal imaging, or intravital microscopy.

In another embodiment, the presence, absence or level of the compound's fluorescence is indicative of a disease state.

In another embodiment, the disease state is Alzheimer's disease.

In another embodiment, the subject is a living animal.

In another embodiment, the subject is a human.

In another embodiment, the compound is administered via intravenous (IV) injection.

In another embodiment, L is —CH=CH—(CO)—CH=C(OH)—CH=CH— or —CH=CH—(CO)—CH$_2$—C(O)—CH=CH—.

In another embodiment, $Ar^1$ and $Ar^2$ are independently selected from

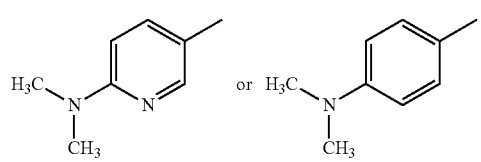

In a preferred embodiment, the compound has the structure:

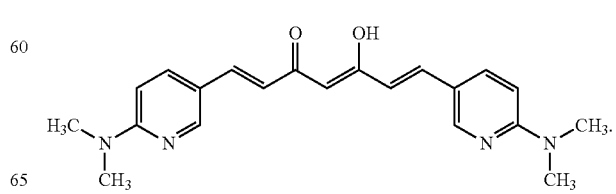

In another embodiment, L is

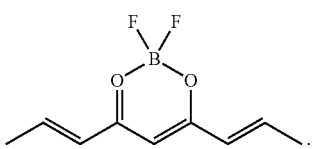

In another embodiment, Ar[1] and Ar[2] are independently selected from

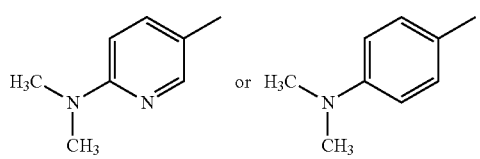

In another preferred embodiment, the compound has the structure:

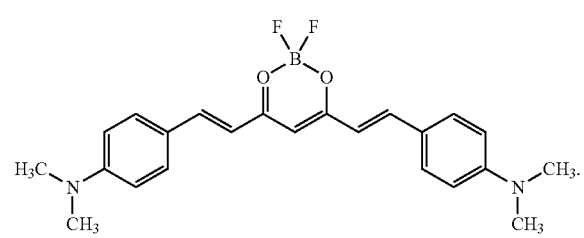

In another embodiment, Ar[1] and Ar[2] are independently selected from

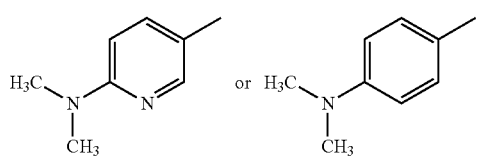

In another aspect, the present invention provides a method for providing an image of soluble amyloid beta contained within a subject by positron emission tomography (PET) scan, comprising (a) administering to a subject a $^{11}$C or $^{18}$F labeled derivative of a compound having the formula Ar[1]-L-Ar[2]; and (b) imaging gamma rays are emitted due to the compound bound to the soluble amyloid beta within the subject in order to provide an image of the soluble amyloid beta contained in the subject. L is a divalent linking group comprising an alkenylene having 5 to 15 backbone carbon atoms, wherein at least two of the backbone carbon atoms form part of a carbonyl or secondary alcohol and Ar[1] and Ar[2] are each independently alkyl amine-substituted aryl or heteroaryl groups; or L is a divalent linking group comprising an alkenylene having 5 to 15 backbone carbon atoms, wherein at least two of the backbone carbon atoms form part of a difluoroboronate ring; and Ar[1] and Ar[2] are each independently alkyl amine-substituted aryl or heteroaryl groups. The compound binds soluble amyloid beta contained in the subject.

In one embodiment, the presence, absence or level of the compound within the subject is indicative of a disease state.

In another embodiment, the disease state is Alzheimer's disease.

In another embodiment, L is —CH═CH—(CO)—CH═C (OH)—CH═CH— or —CH═CH—(CO)—CH$_2$—C(O)—CH═CH—.

In another embodiment, Ar[1] and Ar[2] are independently selected from

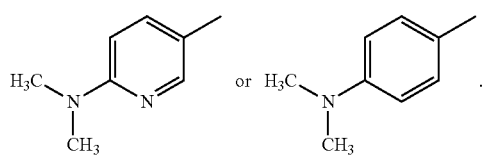

In a preferred embodiment, the compound has the structure:

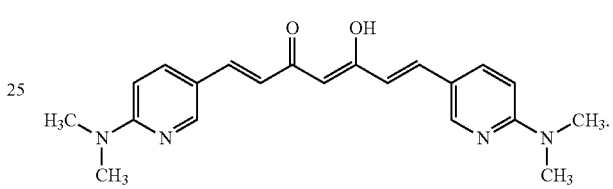

In another embodiment, L is

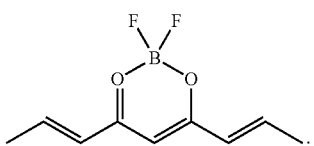

In another embodiment, Ar[1] and Ar[2] are independently selected from

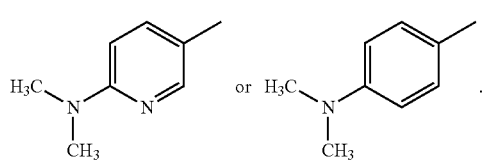

In another preferred embodiment, the compound has the structure:

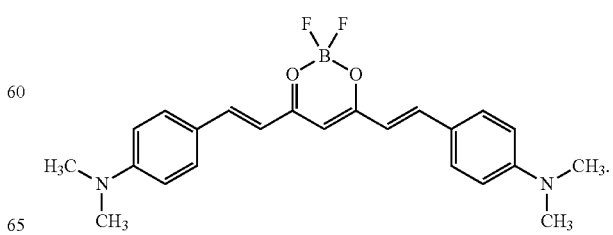

In another embodiment, Ar$^1$ and Ar$^2$ are independently selected from

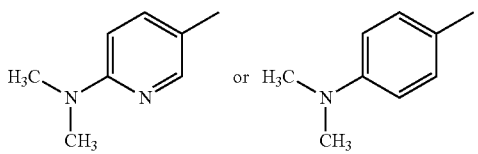

In another aspect, the present invention provides a method for providing an image of soluble amyloid beta contained within a subject by magnetic resonance imaging, comprising (a) administering to a subject a $^{19}$F labeled derivative of a compound having the formula Ar$^1$-L-Ar$^2$ and (b) imaging the subject in order to obtain a magnetic resonance image of the compound bound to the soluble amyloid beta and contained within the subject. L is a divalent linking group comprising an alkenylene having 5 to 15 backbone carbon atoms, wherein at least two of the backbone carbon atoms form part of a carbonyl or secondary alcohol and Ar$^1$ and Ar$^2$ are each independently alkyl amine-substituted aryl or heteroaryl groups or L is a divalent linking group comprising an alkenylene having 5 to 15 backbone carbon atoms, wherein at least two of the backbone carbon atoms form part of a difluoroboronate ring; and Ar$^1$ and Ar$^2$ are each independently alkyl amine-substituted aryl or heteroaryl groups. The compound binds soluble amyloid beta contained in the subject.

In one embodiment, the presence, absence or level of the compound within the subject is indicative of a disease state.

In another embodiment, the disease state is Alzheimer's disease.

In another embodiment, L is —CH=CH—(CO)—CH=C (OH)—CH=CH— or —CH=CH—(CO)—CH$_2$—C(O)—CH=CH—.

In another embodiment, Ar$^1$ and Ar$^2$ are independently selected from

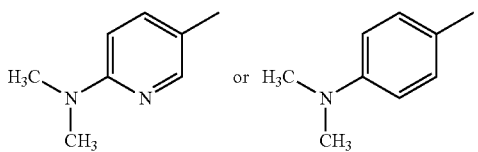

In a preferred embodiment, the compound has the structure:

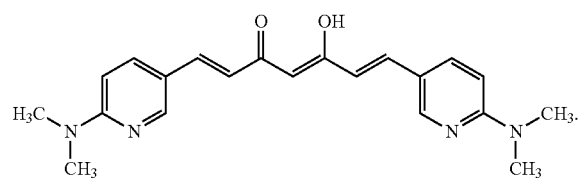 [SMILES: CN(C)c1ccc(/C=C/C(=O)/C=C(O)/C=C/c2ccc(N(C)C)nc2)cn1]

In another embodiment, L is

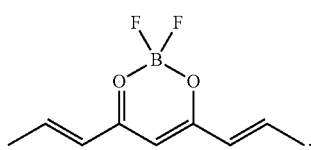

In another embodiment, Ar$^1$ and Ar$^2$ are independently selected from

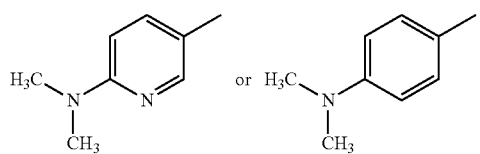

In another preferred embodiment, the compound has the structure:

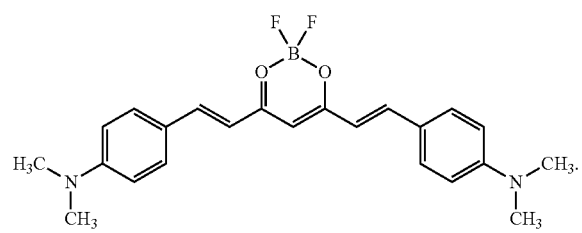

In another embodiment, Ar$^1$ and Ar$^2$ are independently selected from

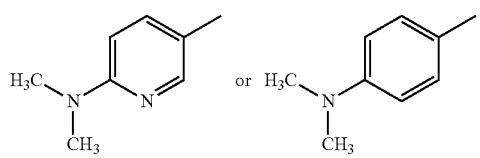

In another aspect, the present invention provides an optical system for imaging soluble amyloid beta in a sample, comprising (a) a fluorescence excitation source for illuminating at least a portion of the sample, the fluorescence excitation source configured to excite fluorescent emission of a compound having the formula Ar$^1$-L-Ar$^2$; (b) a fluorescence light detector for detecting fluorescent light emitted by the compound bound to soluble amyloid beta; and (c) an imaging means to provide an image of the compound in the sample which correlates to soluble amyloid beta present in the sample. L is a divalent linking group comprising an alkenylene having 5 to 15 backbone carbon atoms, wherein at least two of the backbone carbon atoms form part of a carbonyl or secondary alcohol and Ar$^1$ and Ar$^2$ are each independently alkyl amine-substituted aryl or heteroaryl groups, or L is a divalent linking group comprising an alkenylene having 5 to 15 backbone carbon atoms, wherein at least two of the backbone carbon atoms form part of a difluoroboronate ring; and Ar$^1$ and Ar$^2$ are each independently alkyl amine-substituted aryl or heteroaryl groups. The compound binds soluble amyloid beta in the sample.

In one embodiment, the fluorescence excitation source comprises a laser or light-emitting diode.

In another embodiment, the fluorescence light detector comprises a charge coupled device (CCD) system or photographic film.

In another embodiment, the fluorescence excitation source and the fluorescence light detector are embodied in an endoscopic device, a catheter-based device, a diffuse optical tomographic imaging device, a phased array technology device, a confocal imaging device, or an intravital microscopy device.

In another embodiment, the method is carried out in an vitro setting.

In another embodiment, the method is carried out in an in vivo setting.

In another aspect, the present invention provides use of a compound having the formula designated CRANAD-2, CRANAD-3, CRANAD-5 in FIG. 1, or a derivative or analog thereof, for the manufacture of an injectable dosage for the in vivo imaging of soluble amyloid beta in a subject.

In another aspect, the present invention provides a compound having the formula designated CRANAD-2, CRANAD-3, CRANAD-5 in FIG. 1, or a derivative or analog thereof, for use in in vivo imaging of soluble amyloid beta in a subject.

Other objects, features and advantages of the present invention will become apparent after review of the specification, claims and drawings.

DETAILED DESCRIPTION OF THE INVENTION

I. In General

Figure 1:
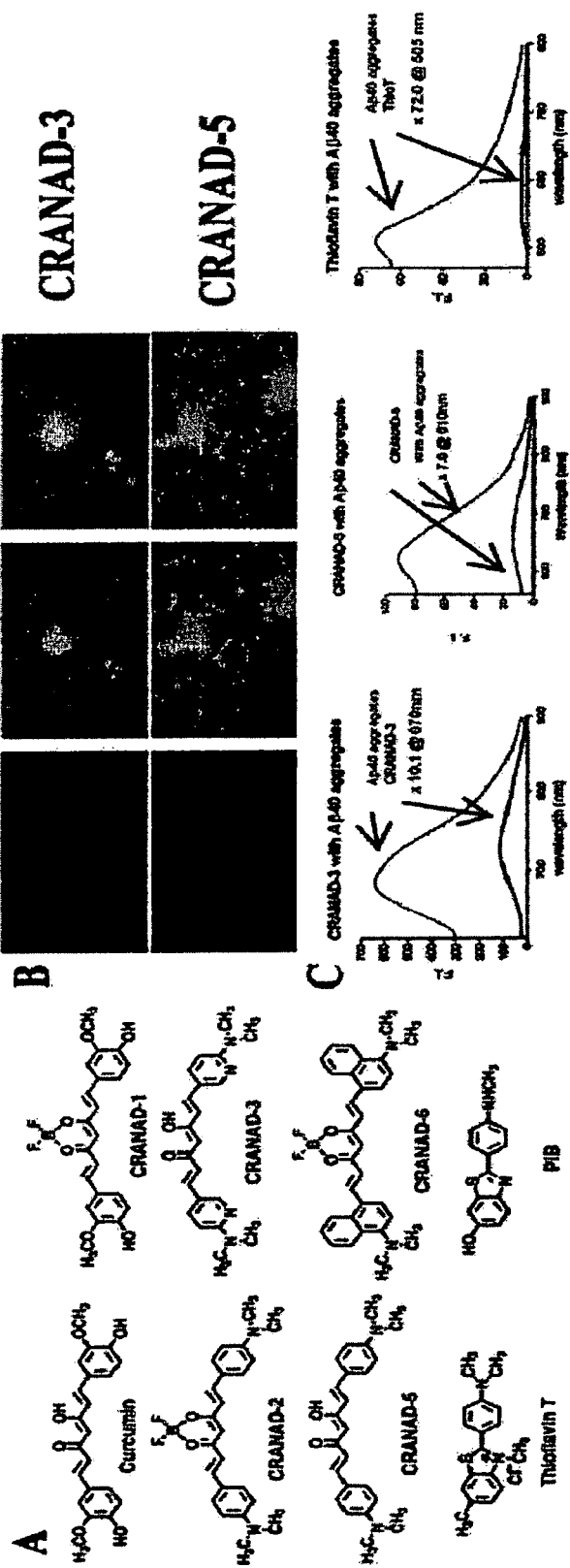
FIG. 1 depicts (A) the chemical structures of compounds tested; (B) histology of CRANAD-3 and CRANAD-5 with APP-PS1 brain section, left: CRANAD-3 or CRANAD-5 staining; middle: thioflavin T; right: merge (40×); (C) fluorescence spectrum of CRANAD-3, 5 and thioT in absence of and in presence of Aβ40 aggregates.

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by any later-filed nonprovisional applications.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. The terms "comprising" and variations thereof do not have a limiting meaning where these terms appear in the description and claims. Accordingly, the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The terminology as set forth herein is for description of the embodiments only and should not be construed as limiting of the invention as a whole. Unless otherwise specified, "a," "an," "the," and "at least one" are used interchangeably and mean one or more than one.

As used herein, the term "organic group" is used for the purpose of this invention to mean a hydrocarbon group that is classified as an aliphatic group, cyclic group, or combination of aliphatic and cyclic groups (e.g., alkaryl and aralkyl groups). In the context of the present invention, suitable organic groups for curcumin derivatives of this invention are those that do not interfere with the curcumin derivatives imaging activity. In the context of the present invention, the term "aliphatic group" means a saturated or unsaturated linear or branched hydrocarbon group. This term is used to encompass alkyl, alkenyl, and alkynyl groups, for example.

As used herein, the terms "alkyl", "alkenyl", and the prefix "alk-" are inclusive of straight chain groups and branched chain groups and cyclic groups, e.g., cycloalkyl and cycloalkenyl. Unless otherwise specified, these groups contain from 1 to 20 carbon atoms, with alkenyl groups containing from 2 to 20 carbon atoms. In some embodiments, these groups have a total of at most 10 carbon atoms, at most 8 carbon atoms, at most 6 carbon atoms, or at most 4 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

The term "heterocyclic" includes cycloalkyl or cycloalkenyl non-aromatic rings or ring systems that contain at least one ring heteroatom (e.g., O, S, N).

Unless otherwise specified, "alkylene" and "alkenylene" are the divalent forms of the "alkyl" and "alkenyl" groups defined above. The terms, "alkylenyl" and "alkenylenyl" are used when "alkylene" and "alkenylene", respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-". Examples of suitable haloalkyl groups are difluoromethyl, trifluoromethyl, and the like. Halogens are elements including chlorine, bromine, fluorine, and iodine.

The term "aryl" as used herein includes monocyclic or polycyclic aromatic hydrocarbons or ring systems. Examples of aryl groups include phenyl, naphthyl, biphenyl, fluorenyl and indenyl. Aryl groups may be substituted or unsubstituted. Aryl groups include aromatic annulenes, fused aryl groups, and heteroaryl groups. Aryl groups are also referred to herein as aryl rings.

Unless otherwise indicated, the term "heteroatom" refers to the atoms O, S, or N.

The term "heteroaryl" includes aromatic rings or ring systems that contain at least one ring heteroatom (e.g., O, S, N). In some embodiments, the term "heteroaryl" includes a ring or ring system that contains 2 to 12 carbon atoms, 1 to 3 rings, 1 to 4 heteroatoms, and O, S, and/or N as the heteroatoms. Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The terms "arylene" and "heteroarylene" are the divalent forms of the "aryl" and "heteroaryl" groups defined above. The terms "arylenyl" and "heteroarylenyl" are used when "arylene" and "heteroarylene", respectively, are substituted. For example, an alkylarylenyl group comprises an arylene moiety to which an alkyl group is attached.

The term "fused aryl ring" includes fused carbocyclic aromatic rings or ring systems. Examples of fused aryl rings include benzo, naphtho, fluoreno, and indeno.

The term "annulene" refers to aryl groups that are completely conjugated monocyclic hydrocarbons. Examples of annulenes include cyclobutadiene, benzene, and cyclooctatetraene. Annulenes present in an aryl group will typically have one or more hydrogen atoms substituted with other atoms such as carbon.

When a group is present more than once in any formula or scheme described herein, each group (or substituent) is independently selected, whether explicitly stated or not. For example, for the formula —C(O)NR$_2$ each of the two R groups is independently selected.

As a means of simplifying the discussion and the recitation of certain terminology used throughout this application, the terms "group" and "moiety" are used to differentiate between chemical species that allow for substitution or that may be substituted and those that, in the particular embodiment of the invention, do not so allow for substitution or may not be so substituted. Thus, when the term "group" is used to describe a chemical substituent, the described chemical material includes the unsubstituted group and that group with nonperoxidic O, N, S, Si, or F atoms, for example, in the chain as well as carbonyl groups or other conventional substituents. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, tert-butyl, and the like.

The invention is inclusive of the compounds described herein (including intermediates) in any of their pharmaceutically acceptable forms, including isomers (e.g., diastereomers and enantiomers), tautomers, salts, solvates, polymorphs, prodrugs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

"Pharmaceutically acceptable" as used herein means that the compound or composition or carrier is suitable for administration to a subject to achieve the treatments described herein, without unduly deleterious side effects in light of the necessity of the treatment.

II. The Invention

Curcumin (diferuloylmethane, 1,7-bis(4-hydroxy-3-methoxyphenyl)-1,6-heptadiene-3,5-dione), a brightly colored powder, is the principal curcuminoid of the Indian curry spice turmeric, and has been consumed daily for thousand of years in India and other regions. Curcumin contains two aryl rings separated by an unsaturated seven carbon spacer having two carbonyls. The aryl rings of curcumin contain a hydroxyl group in the para position and a methoxy group in the meta position. As such, curcumin is a symmetrical diphenolic dienone. It exists in solution as an equilibrium mixture of the symmetrical dienone (diketo) and the keto-enol tautomer; the keto-enol form is strongly favored by intramolecular hydrogen bonding.

Curcumin is known for its antitumor, antioxidant, antiarthritic and anti-inflammatory properties. It has been utilized as an anti-amyloid agent as well. In 2004, it was reported that curcumin could be used as a histological staining reagent for senile plaques and showed that curcumin could decrease amyloid deposits in vivo. Further, it has been demonstrated by two-photon imaging, that curcumin could be visualized in vivo and could prevent the progress of amyloid plaque forming in APP/Tau transgenic mice model. In addition, it is known that curcumin derivatives are suitable for amyloid deposit monitoring by PET. Studies have demonstrated that curcumin is very specific for amyloid plaque and displays high affinity binding for Aβ aggregates. However, curcumin is not practical for in vivo NIR imaging because of its short emission wavelength and low lipophilicity (log P<2).

In this invention, the inventors provide the design, synthesis and testing of a family of novel "smart" NIR Aβ fluorescent probes which open a wide window for new types of NIR fluorescent dyes for cell, tissue, and in vivo imaging. The probes disclosed herein are useful for detecting both soluble Aβ and insoluble Aβ. As such, the probes have potential for monitoring the full course of AD amyloidosis pathology. The probes are useful research tools for both animal and human studies, and may certainly serve as a clinical diagnostic agents. As the probes appear to have wide applicability as fluorescent dyes for biological studies, they are also straight forward to adapt to clinical PET and MRI applications for AD diagnosis.

In terms of "smart" probes, the inventors demonstrate that by modifying curcumin's structure it is possible to shift derivative compounds' emission wavelength to an ideal range for NIR imaging, which spans from 600 nm to 900 nm. The invention therefore provides methods based on unique probes which exhibit significant fluorescence property changes upon binding. In addition, derivative compounds are provided having improved lipophilicity relative to curcumin. Accordingly, the inventors provide a series of curcumin-based compounds that had specific binding abilities to a wide span of Aβ species from the insoluble plaques and aggregates down to the soluble monomeric Aβ40 and Aβ42 peptides, even to the short core fragment (KLVFF) of the peptides.

In particular, the inventors have demonstrated that exemplary compounds CRANAD-2, CRANAD-3 and CRANAD-5 (illustrated in FIG. 1) were able to not only detect plaques in tissue and Aβ aggregates in solution, but also to bind to the monomers, and to sense the fragments of the Aβ peptide. In contrast, thioflavin T showed specificity only to Aβ aggregates, but no significant fluorescence intensity change upon mixing with monmeric Aβ peptide or segments of Aβ peptide. These data were confirmed by reports that thioflavin T was not able to detect soluble Aβ 40/42. The inventors confirmed that the compounds designated CRANAD-2, 3, and 5 were capable of detecting both insoluble and soluble Aβ species in vitro, with further utility as PET version and MRI versions of these probes capable of detecting both insoluble and soluble Aβ species in vivo. Therefore, the present invention provides reagents and methods useful to monitor the full course of AD amyloidosis pathology.

In one particular embodiment, a probe according to the invention was designed by incorporating a difluoroborate ring into curcumin (FIG. 1; hereafter "CRANAD-2"). This probe is the first example of difluoroborate diketone family as imaging probe. This particular probe, exemplary of the invention, is an ideal NIR probe for detecting both Aβ aggregates and soluble species. First, the probe's molecular weight is only 400 dalton. Its log P is 3.0, which is within the range for the recommended lipophilicity (log p 2-5) for CNS drugs that have high potential to penetrate brain blood barrier. Second, utilizing a two-step red-pushing strategy, the inventors obtained the compound with fluorescence emission that falls into the ideal "optical window" (650-900 nm) for NIR imaging.

At the same time CRANAD-2 also exhibits a large stoke shift (140 nm in PBS, and 70 nm in PBS with Aβ aggregates). Moreover, CRANAD-2 shows high quantum yield upon binding to aggregates (40%) though its quantum yield was low (0.6%) in PBS buffer. Third, CRANAD-2 exhibits considerable stability in serum in vitro, which was further confirmed in the inventor's in vivo studies. Additionally, CRANAD-2 does not show any significant binding to BSA, the major serum protein component. Fourth, CRANAD-2 possesses high affinity to Aβ aggregates, with the $K_d$ comparable to that of Thioflavin T and NIAD-4, and being significantly higher than AOI 987. Fifth, CRANAD-2 displays specific staining with Aβ plaques from aged transgenic mice brain tissue, indicating that the probe has particular selectivity for Aβ plaques over other components of brain tissue. Sixth, CRANAD-2 displays specific properties of a "smart" probe since its emission wavelength and fluorescence intensity and lifetime were highly sensitive to the binding with Aβ plaques. After binding to Aβ plaques, the probe was "turned on" and displayed 70 folds increase in fluorescence intensity and 60 nm blue-shift, and significant lifetime change upon binding to the aggregates. The term "fluorescence properties" refer to fluorescence intensity properties; the probe will be "turn on" upon interacting with a target, exhibiting "smart" probe properties, or significant fluorescence life time shortening or prolonging. Finally, the inventors demonstrated that CRANAD-2 could be used for early AD detection in an animal model.

In use, the CRANAD-2 probe of the present invention may be used for several purposes. For instance, the described probe is a potential research tool for animal studies; a future diagnosis agent for clinics; a fluorescent dye for biology studies; a potential class of drugs to treat AD; a potential MRI imaging probe for AD diagnosis (e.g., CRANAD-2 containing at least one fluorine atom which is an $^{19}$F isotope); and a potential PET probe for AD diagnosis (e.g., CRANAD-2 containing at least one fluorine atom which is an $^{18}$F isotope or, alternatively, at least one carbon atom which is a $^{11}$C isotope).

Figure 7:
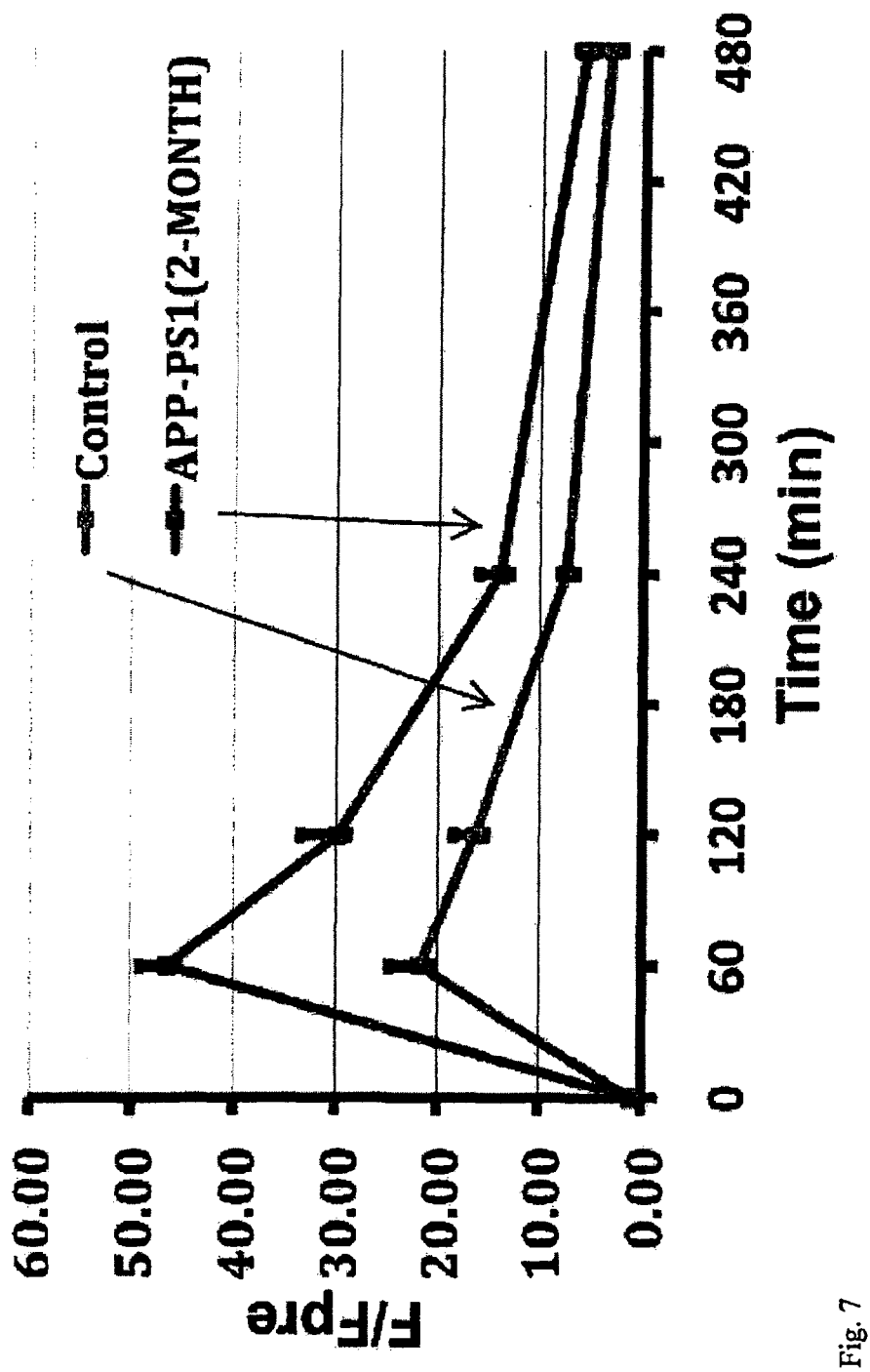
FIG. 7 provides semi-quantitative analysis of the imaging data. Fluorescence signal was normalized to background signal ($F/F_{pre}$) in 2-month old APP-PS1 mice (n=6) and age matched wild-type control mice (n=6).

In another particular embodiment, a probe according to the invention was designed by replacing the phenyl rings of curcumin with pyridyl rings (FIG. 1; hereafter "CRANAD-3"). This probe was able to detect the difference of the Aβ loading at 2-month old in APP-PS1 AD mouse model with NIR imaging. At this age, the Aβ are existing as non-plaque form, in particular, in soluble form. Significant differences between the transgenic group and the control group could be observed from the images and semi-quantitative analysis (FIG. 5C, D and FIG. 7) at 60, 120, 240 min (the difference at 480 min wasn't significant). These data pointed to the feasibility of monitoring the loading of low-molecular weight Aβ species at the very early stage by the exemplary compound CRA-NAD-3.

Figure 6:
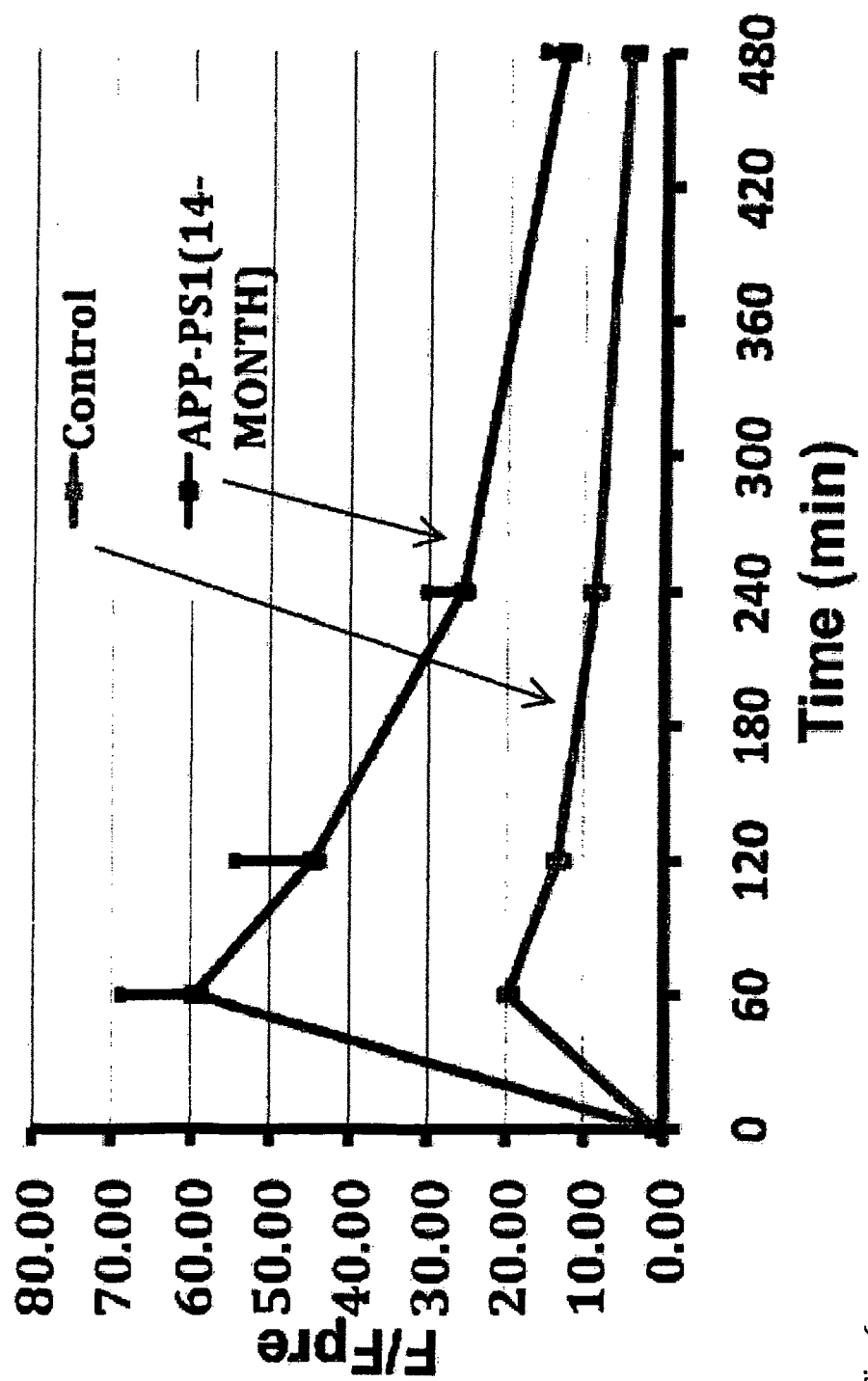
FIG. 6 depicts semi-quantitative analysis of the imaging data. Fluorescence signal was normalized to background signal ($F/F_{pre}$) in 14-month old APP-PS1 mice (n=3) and age matched wild-type control mice (n=3).

Moreover, the normalized signals of CRANAD-3 ($F_{(t)}/F_{(pre)}$) in 14-month APP-PS1 mice were considerably higher than that of the control group at all time points, i.e. 59.59 vs 19.75, 44.70 vs 13.42, 25.67 vs 8.57, and 12.86 vs 4.50 at 60, 120, 240 and 480 min respectively (FIG. 6). At this age, the Aβ species are mainly existing as insoluble form. These data indicated that CRANAD-3 and similar compounds according to the invention are useful as an in vivo NIR probe for monitoring the Aβ plaques in AD mouse model.

Figure 8:
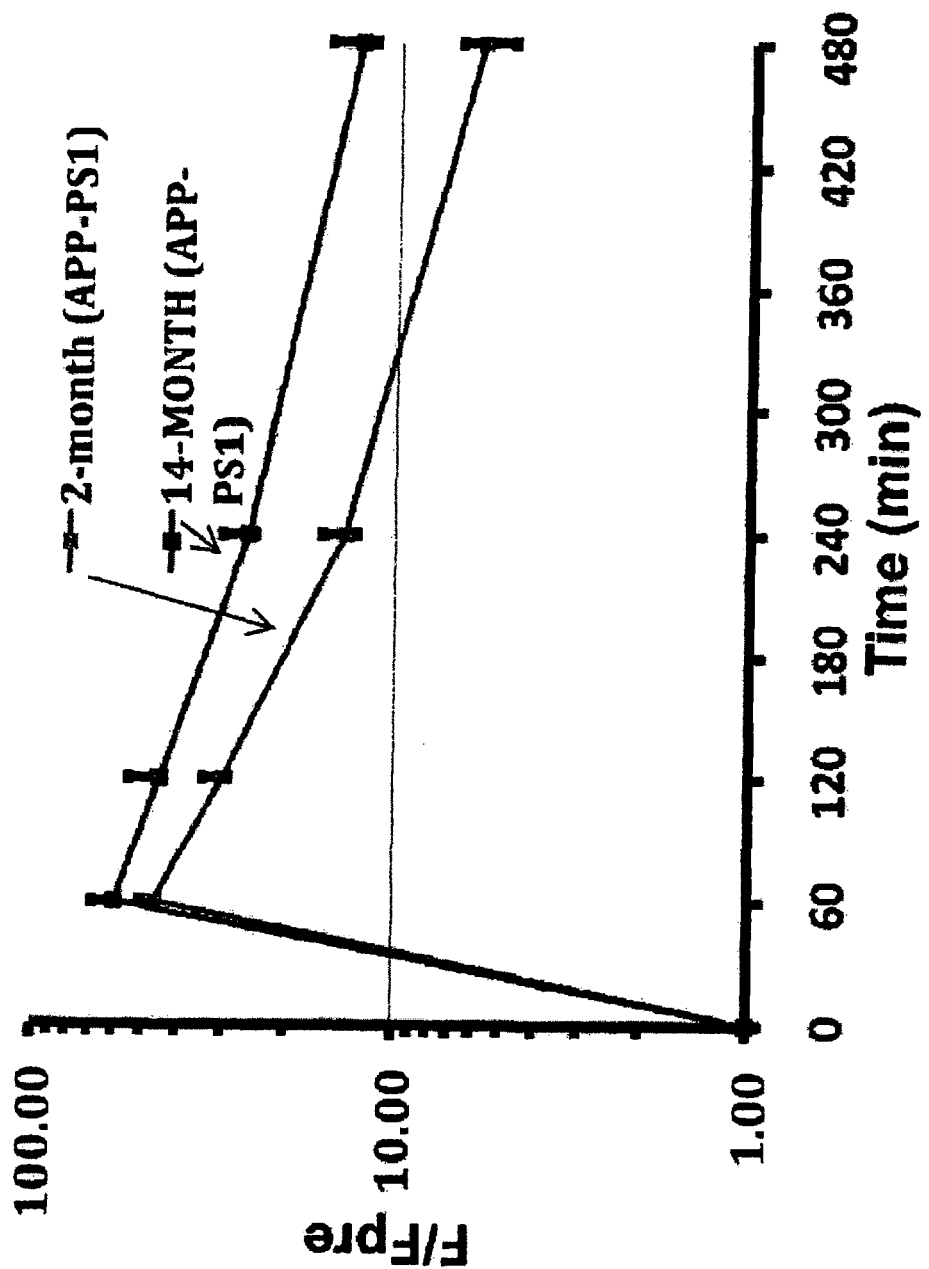
FIG. 8 depicts the normalized fluorescence signal of 14-month (n=3) and 2-month old APP-PS1 mice (n=6). It clearly showed that the signal of 14-month old APP-PS1 was considerably higher than that of 2-month old APP-PS1 mice, and the signal decay of 14-month was significantly slower than that of 2-month old group (Note: Y axis is a Log scale).

Furthermore, the inventors found that the relative signal intensities F(t)/F(pre) of 14-month old transgenic mice were considerably higher than that of 2-month old transgenic mice, while the signal of 14-month and 2-month old controls were similar. By comparing the normalized signals of these two groups of transgenic mice, the inventors observed slower decay of signal in 14-month old group (FIG. 8). Taken together, probes of the invention appear to have the capability to detect the Aβ loading abnormality at the very early stage and to distinguish between the age groups.

Curcumin derivatives are expected to be beneficial for use in the imaging methods of the invention. The term "curcumin derivative" is used interchangeably with the term "curcumin analog" and "curcumin analogue" (alternative spelling) and includes, for example, curcumin derivatives, analogs, curcuminoids and chalcones. In one embodiment, the curcumin derivative includes first and second aryl groups covalently attached by way of a spacer, also referred to herein as a linker or a linking group. In another embodiment, the first and/or second aryl group is a heteroaryl group.

Curcumin derivatives that exhibit improved imaging qualities are preferred. For example, curcumin derivatives that include alkyl amine-substituted aryl or heteroaryl groups and unsaturated spacers are expected to impart improved imaging characteristics. Additional curcumin derivatives not encompassed by the general definition provided above may also be found in the examples and schemes provided herein.

Curcumin derivatives of the invention are generally encompassed by compounds having the formula $Ar^1$-L-$Ar^2$, wherein: (a) L is a divalent linking group comprising an alkenylene having 5 to 15 backbone carbon atoms, wherein at least two of the backbone carbon atoms form part of a carbonyl or secondary alcohol and $Ar^1$ and $Ar^2$ are each independently alkyl amine-substituted aryl or heteroaryl groups; or (b) L is a divalent linking group comprising an alkenylene having 5 to 15 backbone carbon atoms, wherein at least two of the backbone carbon atoms form part of a difluoroboronate ring; and $Ar^1$ and $Ar^2$ are each independently alkyl amine-substituted aryl or heteroaryl groups.

Curcumin derivatives of the invention include aryl or heteroaryl group $Ar^1$, which is positioned at an end of the linker L. Curcumin derivatives of the invention include a second aryl or heteroaryl group $Ar^2$ that is independently selected from $Ar^1$, which is positioned at the other end of the linker L. Preferred aryl or heteroaryl groups include phenyl groups, naphthyl groups, thienyl groups, and pyridinium groups.

Aryl or heteroaryl groups $Ar^1$ and $Ar^2$ are preferably substituted with an amine group, more preferably an alkyl amine group. Additional substituents may be present on the aryl or heteroaryl groups, wherein the ring positions may, independently, be unsubstituted (i.e., R=hydrogen) or one or more R groups may be substituents independently selected from a variety of substituents, including hydroxyl, halogen, alkyl, alkenyl, haloalkyl, alkoxy, amine, carboxyl, and ester substituents. Particularly preferred groups for $Ar^1$ and $Ar^2$ include:

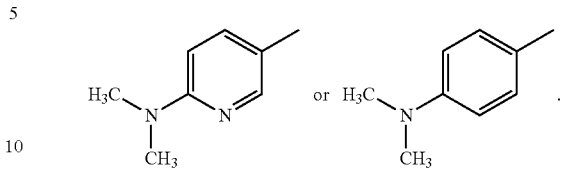

The linker L is a spacer preferably 5-15 carbon atoms in length that form a linear carbon chain connecting the first and second Ar groups. The carbons atoms in the carbon chain that trace out shortest path between the first and second Ar groups are referred to herein as the "backbone" carbon atoms. The number of backbone carbon atoms is readily determined in straight chain alkyl groups. In spacers that include a cyclic alkyl group as a constituent of the linear chain, the backbone carbon atoms include the least number of ring carbons possible. The number of backbone carbon atoms is used herein as a shorthand way to designate the length of the linker being used. For example, a 7-carbon spacer is a divalent spacer that includes 7 backbone carbon atoms. Preferred embodiments of the invention include curcumin derivatives having an odd number of carbon atoms; e.g., 3, 5, and 7-carbon linking groups.

In certain embodiments of the invention, at least one of the backbone carbon atoms is included in a carbonyl (C=O) moiety. The spacer may be substituted or unsubstituted. The spacer may further be saturated or unsaturated. In a preferred embodiment, the spacer contains an odd number of carbon atoms (i.e., 3, 5, or 7 carbon atoms), and alternating unsaturated carbon-carbon bonds. In additional embodiments, the spacer may include a hydroxyl moiety in place of, or in addition to, the at least one carbonyl moiety. Particularly preferred spacers include —CH=CH—(CO)—CH=C(OH)—CH=CH— or —CH=CH—(CO)—CH₂—C(O)—CH=CH—. In other embodiments, at least two carbons of the linker's backbone are involved in forming a difluoroboronate ring structure. A particularly preferred linker of this type is illustrated by the structure:

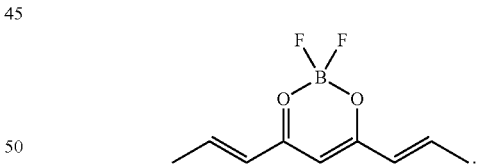

As can be appreciated, curcumin derivatives of the invention preferably include a linking group L that includes an alkenylene group having between 3 and 7 backbone carbon atoms and preferably at least one carbonyl moiety. The linking group may be substituted or unsubstituted, and may be saturated or unsaturated. Preferably, an unsaturated linking group includes conjugated double bonds. Preferably the linking group also contains an odd number of carbon atoms (i.e., 3, 5, or 7 carbon atoms), and at least one unsaturated carbon-carbon bond. In additional embodiments, the linking group may include a hydroxyl moiety in place of, or in addition to, the at least one carbonyl moiety.

A divalent linking group includes two carbons with unfilled valencies that provide valence points where a covalent bond can be formed to an adjacent aryl or heteroaryl group that also includes a carbon with an unfilled valency. Generally, a valence point is represented in a chemical formula by a bond that is shown as not being attached to another group (e.g., CH$_3$—, wherein — represents the valence point).

To further describe and illustrate exemplary compounds of the present invention, various curcumin derivatives of the invention may be represented by the general formula (I):

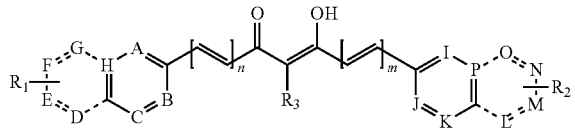

wherein positions A, B, C, D, E, F, G, H, I, J, K, L, M, N, O, and P are independently selected from the atoms C, N, O, or S; n and m are independently 1, 2, or 3; R1 and R2 are each an alkyl amine substituted group; and R3 is an alkyl, N(R$_4$R$_5$), OR$_6$, fluoroalkyl, N(R$_4$)(CH$_2$)nOR$_7$, N(R$_4$)(CH$_2$)nOR$_7$, N(R$_4$)(CH$_2$)n$^{18}$F, N(R$_4$)(CH$_2$)$_n$N(R$_8$R$_9$); N$^{11}$CH$_3$R$_{10}$ (where R$_4$, R$_5$, R$_6$, R$_7$, R$_8$, R$_9$, R$_{10}$ is an alkyl group).

As well, other exemplary curcumin derivatives of the invention are represented by the general formula (II):

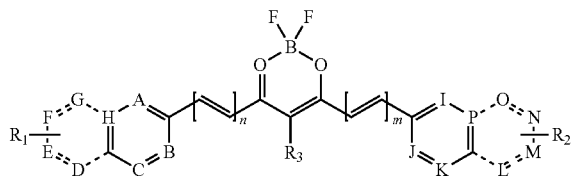

wherein positions A, B, C, D, E, F, G, H, I, J, K, L, M, N, O, and P are independently C, N, O, or S: n and m are independently 1, 2, or 3: R1, R2, are each an alkyl amine substituted group; and R3 is an alkyl, N(R$_4$R$_5$), OR$_6$, fluoroalkyl, N(R$_4$)(CH$_2$)nOR$_7$, N(R$_4$)(CH$_2$)nOR$_7$, N(R$_4$)(CH$_2$)n$^{18}$F, N(R$_4$)(CH$_2$)$_n$N(R$_8$R$_9$); N$_{11}$CH$_3$R$_{10}$ (where R$_4$, R$_5$, R$_6$, R$_7$, R$_8$, R$_9$, R$_{10}$ is an alkyl group).

Particularly preferred compounds according to the invention having demonstrated advantage as "smart" NIR probes include compounds defined by the structures:

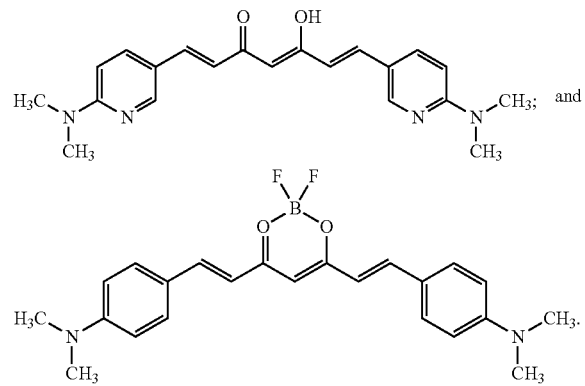

In certain embodiments, the invention provides compounds that are further useful in modalities other than NIR such as postitron emission tomography (PET) or magnetic resonance imaging (MRI). The general formula (III) below illustrates various examples of isotopically-labeled derivatives of the present compounds labeled with the isotopes $^{11}$C, $^{18}$F (for use in PET) or $^{19}$F (for use in MRI).

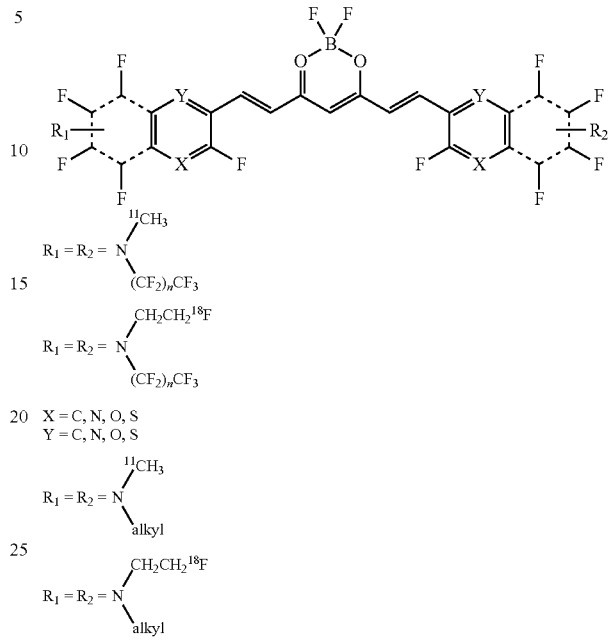

Methods of providing isotopically labeled molecules are well know in the art and the artisan may resort to a variety of known methods to derive isotopically labeled versions of the compounds described and claimed herein. (e.g., see Ryu et al., *J. Med. Chem.* 2006, 6111-6119; Cai et al., *Current Medicinal Chemistry,* 2007, 14, 19-52; and Ametamey et al., *Chem. Rev.,* 2008, 108, 1501-1516.) Accordingly, all isotopically labeled versions of the present compounds accessible through routine labeling procedures are encompassed within the present invention.

Specific methods to synthesize compounds according to the invention are set forth below in the Examples section. Stated generally, compounds of the invention are accessible via the following reaction scheme and general set of reagents:

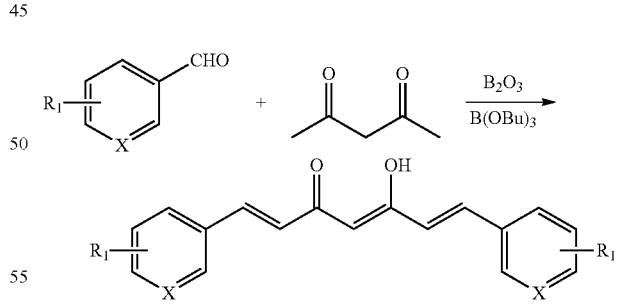

For example, the compound CRANAD-5 is provided where X is carbon and R$_1$ is the group —N(CH$_3$)$_2$. In similar fashion, the compound CRANAD-3 is achieved where X is nitrogen and R$_1$ is the —N(CH$_3$)$_2$ group.

The compounds of the present invention are particularly useful when formulated in the form of a pharmaceutical injectable dosage, including a compound described and claimed herein in combination with an injectable carrier system. As used herein, injectable and infusion dosage forms (i.e., parenteral dosage forms) include, but are not limited to, liposomal injectables or a lipid bilayer vesicle having phospholipids that encapsulate an active drug substance. Injection includes a sterile preparation intended for parenteral use.

Five distinct classes of injections exist as defined by the USP: emulsions, lipids, powders, solutions and suspensions. Emulsion injection includes an emulsion comprising a sterile, pyrogen-free preparation intended to be administered parenterally. Lipid complex and powder for solution injection are sterile preparations intended for reconstitution to form a solution for parenteral use. Powder for suspension injection is a sterile preparation intended for reconstitution to form a suspension for parenteral use. Powder lyophilized for liposomal suspension injection is a sterile freeze dried preparation intended for reconstitution for parenteral use that is formulated in a manner allowing incorporation of liposomes, such as a lipid bilayer vesicle having phospholipids used to encapsulate an active drug substance within a lipid bilayer or in an aqueous space, whereby the formulation may be formed upon reconstitution. Powder lyophilized for solution injection is a dosage form intended for the solution prepared by lyophilization ("freeze drying"), whereby the process involves removing water from products in a frozen state at extremely low pressures, and whereby subsequent addition of liquid creates a solution that conforms in all respects to the requirements for injections. Powder lyophilized for suspension injection is a liquid preparation intended for parenteral use that contains solids suspended in a suitable fluid medium, and it conforms in all respects to the requirements for Sterile Suspensions, whereby the medicinal agents intended for the suspension are prepared by lyophilization. Solution injection involves a liquid preparation containing one or more drug substances dissolved in a suitable solvent or mixture of mutually miscible solvents that is suitable for injection. Solution concentrate injection involves a sterile preparation for parenteral use that, upon addition of suitable solvents, yields a solution conforming in all respects to the requirements for injections. Suspension injection involves a liquid preparation (suitable for injection) containing solid particles dispersed throughout a liquid phase, whereby the particles are insoluble, and whereby an oil phase is dispersed throughout an aqueous phase or vice-versa. Suspension liposomal injection is a liquid preparation (suitable for injection) having an oil phase dispersed throughout an aqueous phase in such a manner that liposomes (a lipid bilayer vesicle usually containing phospholipids used to encapsulate an active drug substance either within a lipid bilayer or in an aqueous space) are formed. Suspension sonicated injection is a liquid preparation (suitable for injection) containing solid particles dispersed throughout a liquid phase, whereby the particles are insoluble. In addition, the product may be sonicated as a gas is bubbled through the suspension resulting in the formation of microspheres by the solid particles.

The parenteral carrier system includes one or more pharmaceutically suitable excipients, such as solvents and co-solvents, solubilizing agents, wetting agents, suspending agents, thickening agents, emulsifying agents, chelating agents, buffers, pH adjusters, antioxidants, reducing agents, antimicrobial preservatives, bulking agents, protectants, tonicity adjusters, and special additives.

In in vivo methods according to the invention, the tolerable dosage for an animal, including a human, is from about 0.001 mg/kg to about 40 mg/kg of a curcumin derivative described herein. Specifically, for NIR imaging, the preferable dosage is from about 1.0 mg/kg to about 10.0 mg/kg; for PET imaging, the dosage is from about 0.001 mg/kg to about 0.1 mg/kg; for MRI imaging, the dosage is from about 1.0 mg/kg to about 40 mg/kg.

In yet other embodiments, the invention encompasses optical systems for detecting soluble amyloid beta in a sample via the NIR modality. Such systems include: (a) a fluorescence excitation source for illuminating at least a portion of the sample, the fluorescence excitation source configured to excite fluorescent emission of a curcumin derivative described herein that is contacted with the sample to bind soluble amyloid beta present in the sample; (b) a fluorescence light detector for detecting fluorescent light emitted by the compound; the fluorescent light correlated to soluble amyloid beta present in the subject.

Suitable fluorescence excitation sources include, e.g., a laser or light-emitting diode. As well, suitable fluorescence light detectors may be in the form of, e.g., a charge coupled device (CCD) system or photographic film. In certain embodiments, the fluorescence excitation source and the fluorescence light detector are embodied in an endoscopic device, a catheter-based device, a diffuse optical tomographic imaging device, a phased array technology device, a confocal imaging device, or an intravital microscopy device.

The following examples are, of course, offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

III. Examples

Example 1

Methods and Materials

Reagents used for synthesis were purchased from Aldrich without further purification. Column chromatography was performed on silica gel (SiliCycle Inc., 60 Å, 40-63 mm) slurry packed into glass columns. Thioflavin S was purchased from Aldrich. Synthetic amyloid-b protein (1-40) was purchased from rPeptide (Bogart, Ga., 30622), and aggregates for in vitro studies were generated following the reported procedure. BSA was purchased from Sigma, and human serum was obtained from Invitrogen (type AB). $^1$H and $^{13}$C NMR spectra were recorded at 400 MHz and 100 MHz respectively and are reported in ppm downfield from tetramethylsilane. Fluorescence studies were carried out with a F-4500 Fluorescense Spectrophotometer. Fluorescence quantum yields were determined using an aqueous solution of Cy5.5-maleimide as a standard (y=0.23). High resolution mass spectra were obtained at the Harvard University, Department of Chemistry Instrumentation Facility. Transgenic Tg2576 mice {-45} and littermates were purchased from Taconic Farm, Balb/c mice for BBB penetrating test were obtained from Jackson Laboratory, and the experiment procedure was approved by Massachusetts General Hospital. In vivo imaging was recorded on Kodak Imaging Station 2000MM.

Synthesis of CRANAD-1 and CRANAD-2

The synthesis of CRANAD-1 was performed according to the reported procedure. (Weber, et al., *Bioorg. Med. Chem.* 2005, 13:3811-20). Synthesis of CRANAD-2 (2,2-difluoro-1,3-dioxaboryl-pentadione) was performed according to the following procedure: 1,3-pentadione (0.1 g, 1.0 mmol) and trifluoroboron ether (0.2 g, 1.0 mmol) were mixed together, and the resulting solution was heated at 60° C. for 2 h. After cooling to room temperature, the reaction mixture was subjected to evaporation under vacuum, and a yellow, pale semisolid was obtained, which solidified to a yellow, pale needle crystal upon standing at room temperature. The above crystals (0.15 g, 0.1 mmol) were dissolved in acetonitrile (3.0 ml). Triethylamine (0.30 g, 3.0 mmol) was added to the above solution, followed by 4-N,N-dimethyl-benzaldehyde (0.30 g, 2.0 mmol). The resultant was stirred at 60° C. overnight. After removing the solvent a black residue was obtained and subjected to flash column chromatography with methylene chloride to give black powder (63.0 mg, yield: 15%). $^1$H NMR (DMSO-d6) δ (ppm) 3.04 (s, 12H), 6.26 (s, 1H), 6.79 (m, 6H), 7.68 (d, 4H, J=8.0 Hz), 7.82 (d, 2H, J=16 Hz); $^{13}$C NMR (DMSO-d6) δ (ppm) 40.3, 100.6, 112.1, 113.3, 121.8, 132.3, 150.3, 153.5; $^{19}$F NMR (DMSO-d6) δ (ppm)–138.9.

Preparation of CRANAD-3 and CRANAD-5 Compounds

CRANAD-5: The synthesis followed the reported procedure with some modifications. Venkateswarlu, et al., *Biorg. Med. Chem.* 2005, 13(23): 6374-6380). Boric oxide (700.0 mg, 10.0 mmol) was dissolved in DMF (10.0 mL) at 120° C. Ensuring most of the boric oxide dissolved was very crucial to obtain a high yield. Acetylacetone (1.1 mL, 10.0 mmol) was added to this solution, followed by tributyl borate (5.4 mL, 20.0 mmol) at 110° C. The solution was stirred for 5 min. 4-N,N'-dimethylamino-benzaldehyde (3.1 g, 20.0 mmol) was added to the above borate complex and stirred for 5 min. A mixture of 1,2,3,4-tetrahydroquinoline (0.2 mL) and acetic acid (0.4 mL) in DMF (4.0 mL) was added to the reaction mixture and heated to 110° C. for 2 h. After cooling to room temperature, the reaction mixture was poured into ice-water (500 mL), and the reddish precipitate was collected, which was further purified by silica gel column using ethyl acetate/hexanes (50:50) as eluent to give CRANAD-5 (1.8 g). $^1$H NMR (DMSO-d6) δ; 13C NMR (DMSO-d6) δ (ppm). $^1$H NMR (CDCl$_3$) δ (ppm) 3.03 (s, 6H), 5.73 (s, 1H), 6.42 (d, 2H, J=16.0 Hz), 6.68 (d, 4H, J=10.0 Hz), 7.45 (d, 4H, J=10.0 Hz), 7.60 (d, 2H, J=16.0 Hz); $^{13}$C NMR (CDCl$_3$) δ (ppm) 40.4, 101.1, 112.1, 119.4, 123.3, 130.0, 140.8, 151.8, 183.6. The spectra were consistent with the reported value.

CRANAD-3: The synthesis of the immediate material (2,2-difluoro-1,3-dioxaboryl-pentadione) was performed using a modified procedure (Ran et al. *J. Am. Chem. Soc.* 2009, 131, 15257-61). The above immediate compound (0.15 g, 0.1 mmol) was dissolved in acetonitrile (3.0 ml), followed by the additions of acetic acid (0.2 ml), tetrahydroisoquinoline (0.04 mL, 0.3 mmol), and 6-N,N'-diethyl-3-pyridylaldehyde (0.36 g, 2.0 mmol). The resultant solution was stirred overnight at 60° C. A black residue was obtained after removing the solvent, and the residue was subjected to flash column chromatography with methylene chloride to give a black powder (63.0 mg, yield: 15.0%). $^1$H NMR (CDCl$_3$) δ (ppm) 1.24 (t, 12H, J=7.2 Hz), 3.58 (q, 8H, J=7.2, 14.0 Hz), 5.89 (s, 1H), 6.42 (d, 2H, J=16.0 Hz), 6.51 (d, 2H, J=9.0 Hz), 7.66 (dd, 2H, J=2.4, 9.0 Hz), 7.92 (d, 2H, J=16.0 Hz), 8.34 (d, 2H, J=5.0 Hz); $^{13}$C NMR (CDCl$_3$) δ (ppm) 18.8, 42.7, 101.6, 106.3, 115.9, 118.6, 136.0, 144.2, 153.4, 159.8, 178.2.

AD Tissue Staining

The inventors conducted tissue staining with 25 micron brain sections from 12-month old APP-PS1 mice stained with all the compounds listed in FIG. 1. As reported, curcumin, PiB, thioflavin T, and CRANAD-2 stained the plaques brightly; while as expected, CRANAD-2, CRANAD-3, and CRANAD-5 yielded good staining as well (FIG. 1B). These data indicate that these compounds are specific to Aβ plaques.

Aβ Aggregates Detection in Solution by Fluorescence Spectrum

The inventors generated Aβ40 aggregates by stirring the solution at room temperature for 3 days, and transmission electron microscopy (TEM) confirmed the existence of aggregates. The inventors then incubated 250 nM of the compounds with 250 nM of Aβ40 aggregates (calculation based on monomers) in PBS for one minute, and then measured the fluorescence spectra of the solutions. The results showed that CRANAD-1 and CRANAD-6 were not "smart" fluorescence probes; while CRANAD-2, 3, 5, curcumin and thioflavin T displayed intensity increases, and CRANAD-2, 3, 5 and curcumin had wavelength blue-shifts as well (FIG. 1C). Compounds that demonstrated a significant intensity increase and/or wavelength shift were deemed to be "smart" probes. Thioflavin T, the standard compound used for assessing the degree of fibrillating, was reported as a "smart" optical probe, and the results were consistent with this claim. Thioflavin T yielded the highest fluorescence intensity (FI) amplification (72-fold), and CRANAD-3 showed the highest FI reading (FIG. 1C). In addition, it was interesting to note that PiB displayed a red-shift and a slight FI decrease. This example illustrates the utility of compounds CRANAD-2, CRANAD-3, and CRANAD-5 as probes for the detection of Aβ plaques.

AD Tissue Staining

The inventors conducted tissue staining with 25 micron brain sections from 12-month old APP-PS1 mice using all the compounds listed in FIG. 1. As reported, curcumin, PiB, thioflavin T and CRANAD2 stained the plaques brightly; while as expected, CRANAD-2, CRANAD-3, and CRANAD-5 yielded good staining as well (FIG. 1B). These data indicate that these compounds are specific to Aβ plaques.

Aβ Aggregates Detection in Solution by Fluorescence Spectrum

Figure 3:
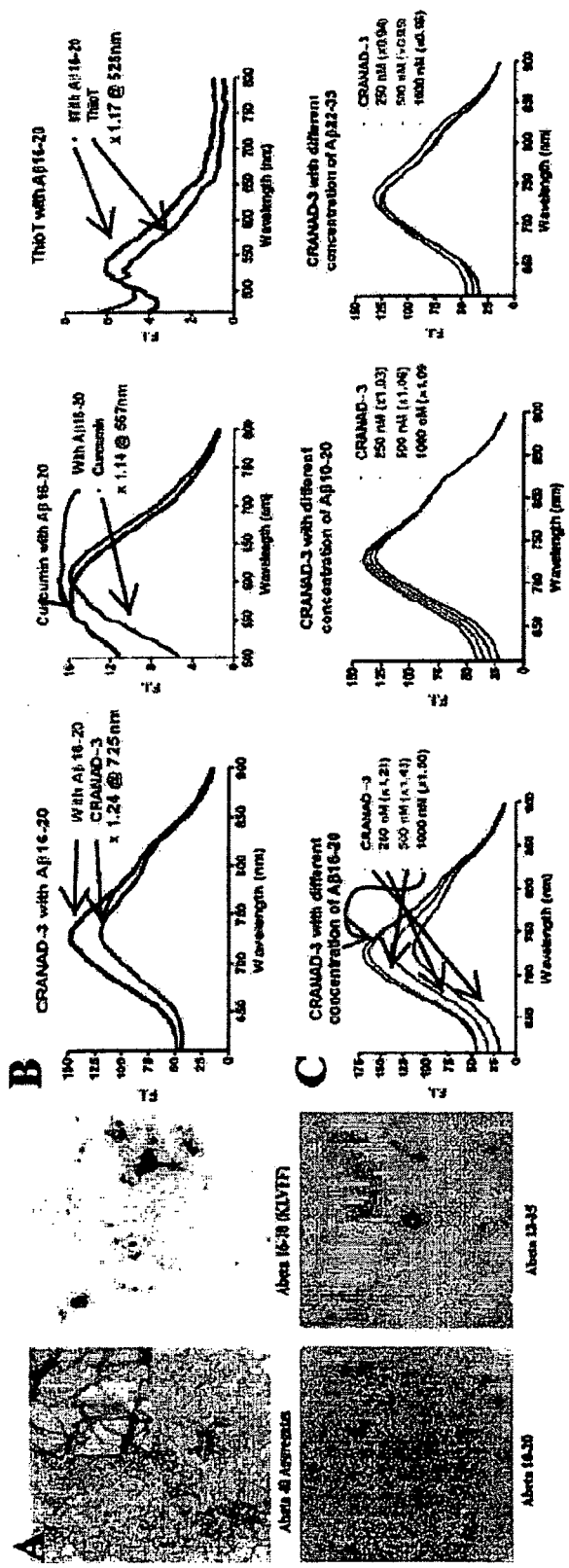
FIG. 3 provides (A) TEM of Aβ40 aggregates, Aβ16-20, Aβ10-20, and Aβ22-35; (B) fluorescence spectrum of CRANAD-3, curcumin, and thioT in absence and in presence of Aβ16-20; (C) different concentrations of CRANAD-3 with different Aβ segments Aβ16-20, Aβ10-20, and Aβ22-35.

The inventors generated Aβ40 aggregates by stirring the solution at room temperature for 3 days, and TEM confirmed the existence of aggregates (FIG. 3A). They incubated 250 nM of the compounds with 250 nM of Aβ40 aggregates (calculation based on monomers) in PBS for one minute, and then measured the fluorescence spectra of the solutions. The results showed that CRANAD-1, and CRANAD-6 were not "smart" fluorescence probes; while CRANAD-2, 3, 5, curcumin, and thioflavin T displayed intensity increases, and CRANAD2, 3, 5, and curcumin had wavelength blue-shifts as well (FIG. 1C). Thioflavin T, the standard compound used for assessing the degree of fibrillating, was reported as a "smart" optical probe, and our results were consistent with this claim. Thioflavin T yielded the highest FI amplification (72-fold), and CRANAD-3 showed the highest FI reading (FIG. 1C). In addition, it was interesting to note that PiB displayed a red-shift and slight FI decrease.

Probes Binding to Dimeric Aβ Dimeric

Dimeric cross-linked Aβ species (CAPS) are highly neurotoxic and are thought to be a key pathological species in AD brain. The inventors tested the binding of their probes to dimeric CAPS. CAPS were generated by incubation of Aβ42 with copper under mild oxidative conditions. Dimerization of Aβ was confirmed by western blot (FIG. 2B) and its non-aggregating morphology was confirmed by TEM. CRANAD-3 and CRANAD-5 had significant F.I. increases (20- and 5-fold respectively) and emission blue-shifts in the presence of dimers. However, thioT and PiB signals were not changed by the addition of dimeric CAPS.

Aβ Monomeric Peptides Detection

Figure 2:
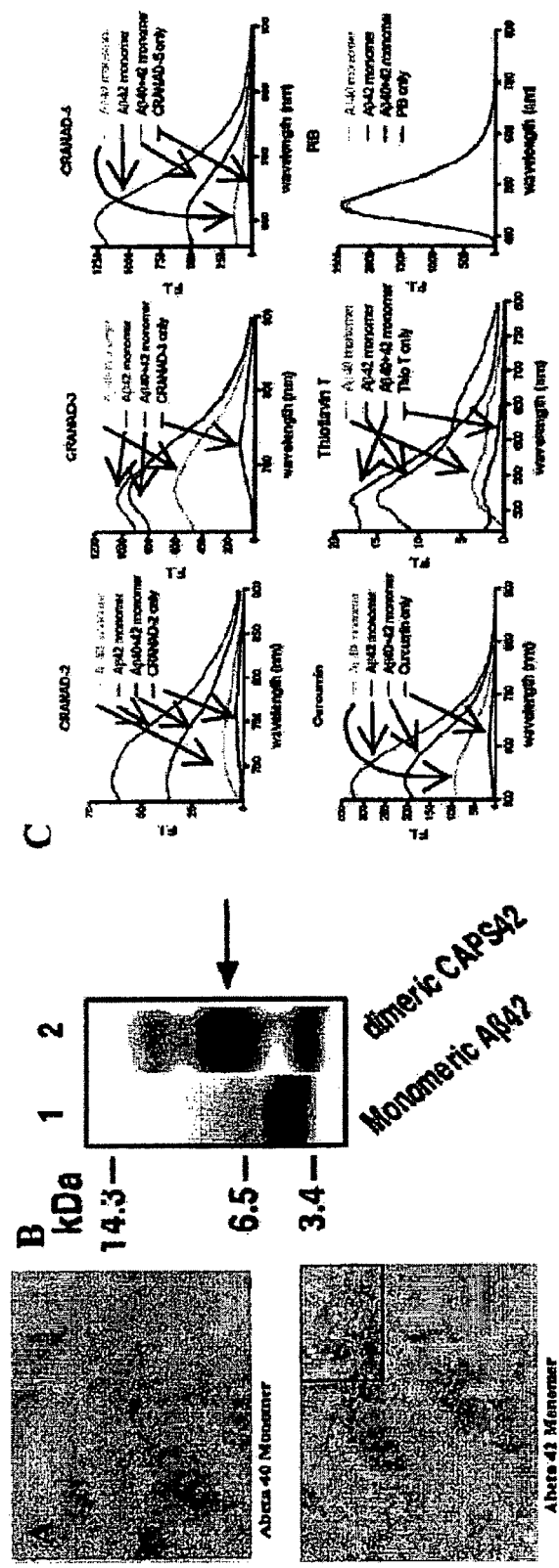
FIG. 2 illustrates (A) TEM of Aβ40 monomer; (B) western blot of Aβ40/42 monomers; (C) fluorescence spectrum of CRANAD-2, 3, 5, curcumin, PiB and thioT in absence of and in presence of Aβ40/42 monomers or Aβ40+Aβ42 monomer (1:1).

Monomeric Aβ40 and Aβ42 peptides were obtained by purification of commercially available synthetic peptides (Done by Dr. Robert Moir group), and their monomeric properties were confirmed by both, SDS-PAGE gel and TEM (FIGS. 2A and B). The inventors incubated the listed compounds (250 nM) with monomeric Aβ40 and Aβ42 (250 nM) in PBS for one min., and then recorded the emission spectra. They found that CRANAD-3 gave the highest amplification (16.8 fold) and the highest fluorescence intensity (FI=610@660 nm) for Aβ40 monomer; while CRANAD-5 was the most sensitive probe for Aβ42 monomer (126.5 fold of amplification @ 600 nm), and also gave the highest fluorescence intensity (FI=1300@600 nm). Meanwhile, CRANAD-2 and curcumin displayed considerable "smartness" upon interaction with Aβ40 and Aβ42 monomer respectively. Moreover, CRANAD2, 3, 5, and curcumin exhibited a clear blue wavelength shift. However, CRANAD-1, CRANAD-6, thioflavin T, and PiB did not show significant intensity amplification or wavelength shift (FIG. 2C). It is noted that all the compounds showed much higher amplification towards Aβ42 monomer than that toward Aβ40 monomer.

Regarding the real in vivo situation, Aβ40 and Aβ42 monomers co-exist; therefore, we tested a 1:1 mixture of the two monomers with the listed compounds, and found the CRANAD-5 was the most sensitive probe in terms of amplification; CRANAD-3 yielded the highest FI reading. The order of the intensity amplification of this mixture was CRANAD-5>CRANAD-2>CRANAD-3>curcumin, and all of these compounds displayed apparent blue-shifts of wavelength. Again, CRANAD-1, CRANAD-6, and PiB did not show significant intensity amplification or wavelength shift (FIG. 2C). Although thioflavin T showed about a 9.0 fold intensity increase, but the FI reading is very low.

Sensing Fragments of Aβ40/42 Peptides

Since our above results already demonstrated that some compounds such as CRANAD-2, CRANAD-3 and CRANAD-5 had clear interaction with monomeric Aβ40/42 peptides, it would be remarkable to pin down the core segment that is necessary for the binding interaction. To that end, the inventors first tested the listed compounds with the most hydrophobic segment Aβ16-20 (KLVFF). Although this segment was normally considered as the core structure for self-assembly aggregation, the KLVFF peptide itself was reported as an aggregation inhibitor. Furthermore, it has been shown that this peptide hardly self-assembles into fibrils, and our TEM results supports this (FIG. 3A). Among the 6 compounds tested, CRANAD-3 displayed the highest FI reading, the highest FI increase (25%), and a 6 nm blue-shift of the emission; while CRANAD-5 showed a new emission peak around 645 nm, and curcumin gave a clear 10 nm blue-shift. All of these changes in fluorescence properties indicated that these compounds had specific interaction with the KLVFF segment (FIG. 3B). As already shown, some compounds had significant changes in fluorescence upon interacting with monomeric Aβ40/42; however, these changes may be partially due to the self-assembly of these monomers in solution. Nonetheless, for the KLVFF peptide, which has much lower aggregating potential than that of monomeric Aβ40/42, it was highly possible that the changes in fluorescence only came from real interaction between the peptide and the compound.

To further confirm that the fluorescence property changes originated from the KLVFF segment, the inventors tested CRANAD-3 with two other Aβ fragments at different concentrations, and ensured by TEM that these peptides were not aggregated. The inventors found that there was no significant change with the non-KLVFF containing peptide Aβ22-35 while there was an apparent FI increase for Aβ10-20, which has the KLVFF motif (FIG. 3C). Based on the above results, the inventors concluded that the KLVFF fragment was the core structure for the interaction.

The in vitro tests demonstrated that compounds CRANAD-2, CRANAD-3, and CRANAD-5 were able to not only detect the plaque in tissue and the Aβ aggregates in solution, but also the dimeric and monomeric Aβ, and the fragments of the Aβ peptide. However, thioflavin T showed specificity only to Aβ aggregates, with no significant fluorescence intensity changes upon mixing with monmeric Aβ peptide and segments of Aβ peptide. These data are supported by reports that thioflavin T and its analogue PIB are not able to detect soluble Aβ 40/42 (H. Mori, 2008). Our data indicated that CRANAD-2, 3, and 5 possess the capacity to detect both insoluble and soluble Aβ species in vitro and in vivo, and it appears that these probes are able to monitor a variety of Aβ species in vivo.

Example 2

Figure 4:
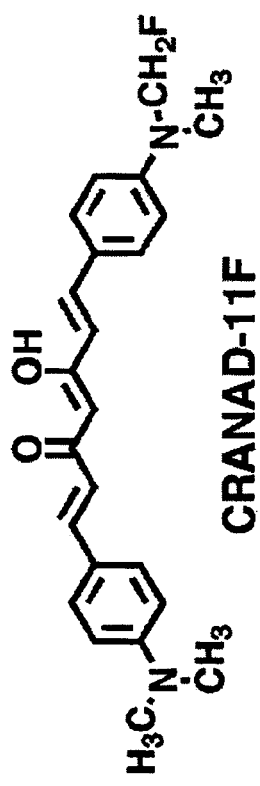
FIG. 4 depicts the chemical structure of an isotopically labeled curcumin derivative according to the invention, CRA-NAD-11F, and that compound's fluorescence intensity bound to Aβ40 monomer versus the unbound compound's fluorescence intensity.
Figure 4:
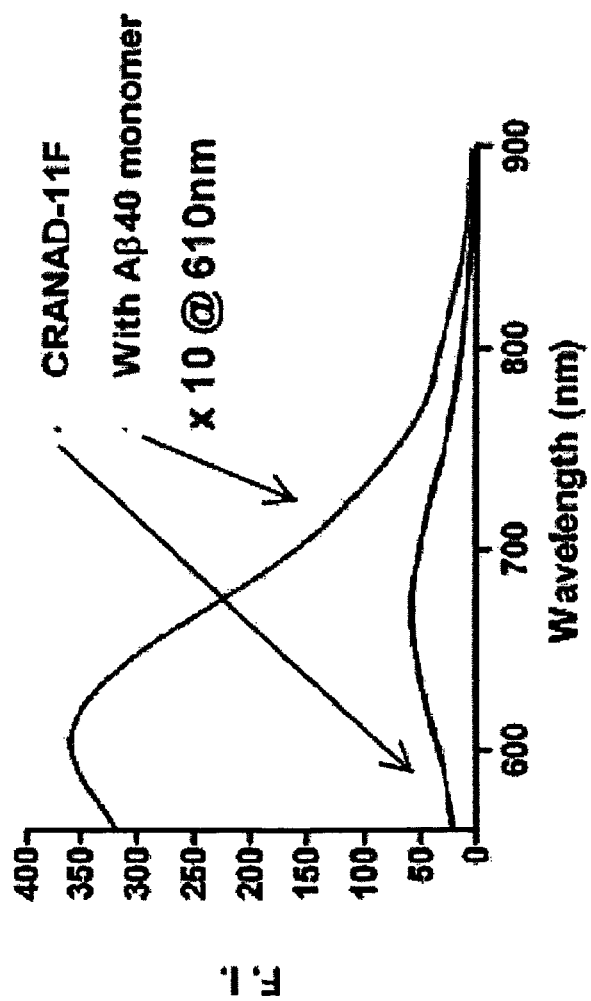

This example describes an isotopically labeled version of CRANAD-5 for use in PET. Specifically, compound CRANAD-11F depicted in FIG. 4 is a radioactive version ($^{18}$F) of a corresponding $^{18}$F PET probe. $^{18}$F isotopically labeled CRANAD-5 was prepared by the following procedure: 1.0 mg $K_2CO_3$ was dissolved in 100 μL water, and this solution was added to a reaction bottle filled with $H^{18}F$ solution. The above mixture was dried by blowing $N_2$ gas. Next, 100 μL of anhydrous DMSO and the precursor of CRANAD-11F (2.0 mg) was added to the dried mixture. This reaction mixture was heated at 140° C. for 5 min. Radioactive TLC indicated that the labeling yield was 40%. CRANAD-11F$^{18}$ was purified by HPLC.

CRANAD-11F, like the smart probes described in the preceding example, displayed specific binding to Aβ40 monomers (see FIG. 4). Note that upon binding to Aβ40 monomers, its fluorescence intensity increased about 10 fold. Therefore, CRANAD-11F is exemplary of compounds according to the invention useful for methods of detecting and monitoring AD pathology.

Example 3

Figure 5:
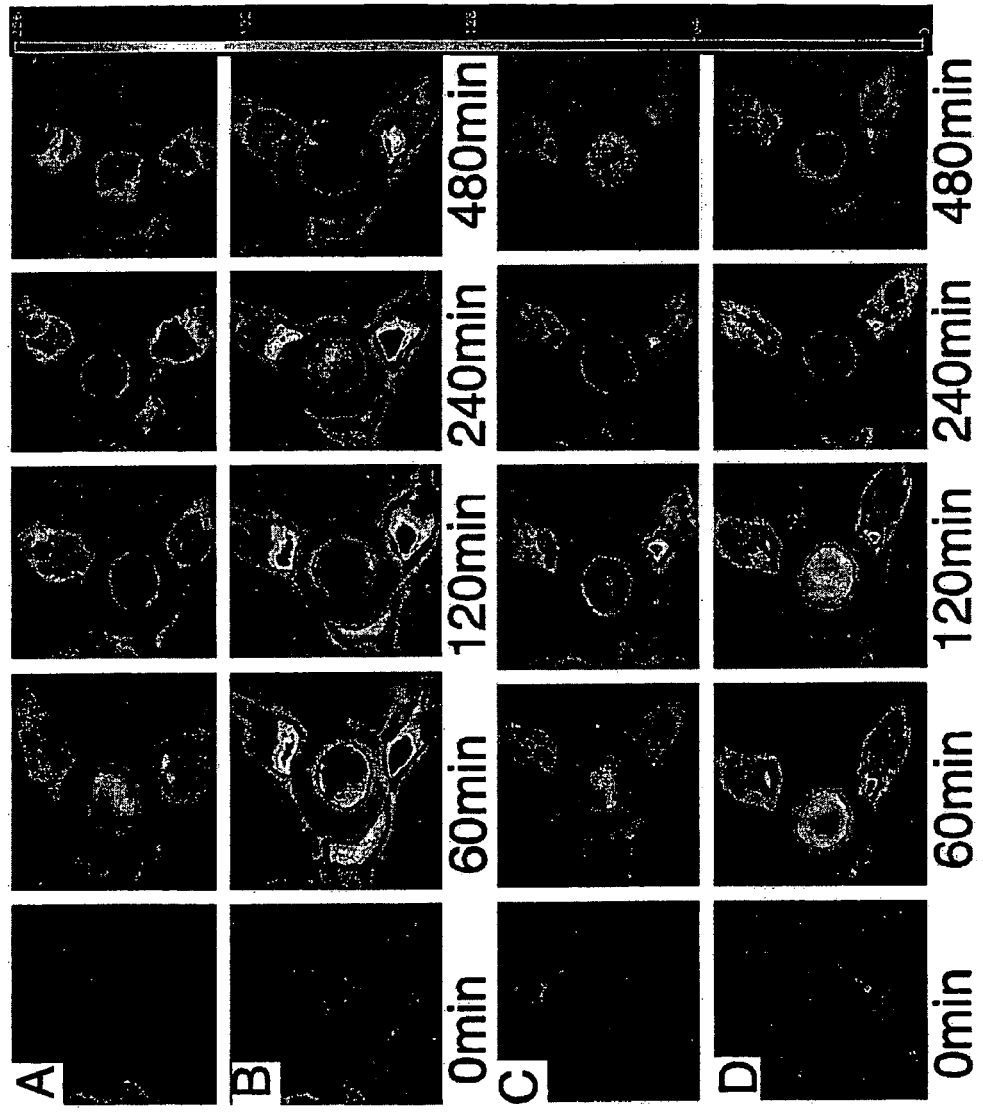
FIG. 5 provides representative images of APP-PS1 and wild-type control mice at different time points before and after i.v. injection of 2.0 mg/kg of CRANAD-3. (A) 14-month old control mouse; (B) 14-month old APP-PS1 mouse; (C) 2-month old control mouse; (D) 2-month old APP-PS1 mouse.

This example describes in vivo imaging performed with a CRANAD-3 probe as illustrated in FIG. 1. Given that CRANAD-3 showed the highest signal and excellent fluorescence intensity amplifying effect for the species tested in vitro, the inventors chose this probe to demonstrate in vivo NIR imaging capabilities of compounds according to the invention. The inventors acquired the images on Kodak Imaging Station 2000MM with Cy3.5 excitation and Cy5.5 emission. First, transgenic 14-month old APP-PS1 mice (n=3) were used to validate the feasibility of CRANAD-3 as a NIR imaging probe. Aged-matched wild-type mice (n=3) served as controls. Images were recorded before and after i.v. injection of CRANAD-3 at 2.0 mg/Kg dosage. The fluorescence intensities of the transgenic group were significantly higher than that of the control group at 60 min, 120 min, 240 min, and 480 min post injection (FIG. 5A, B). Semi-quantitative analysis of the images was performed by selecting a region of interest (ROI) in the brain and normalizing fluorescence intensity at any given time point ($F_{(t)}$) to background fluorescence intensity before the injection ($F_{(pre)}$). As expected, the normalized signals ($F_{(t)}/F_{(pre)}$) in 14-month APP-PS1 mice were considerably higher than that of the control group at all time points, i.e. 59.59 vs 19.75, 44.70 vs 13.42, 25.67 vs 8.57, and 12.86 vs 4.50 at 60, 120, 240 and 480 min respectively (FIG. 6). These data indicated that CRANAD-3 can be used as an in vivo NIR probe for monitoring the amyloidosis pathology in AD mouse model.

Next, because the inventors' in vitro data showed that CRANAD-3 had F.I. amplifying abilities not only for Aβ40 aggregates, but also for Aβ40/42 monomers and dimers, it is reasonable to speculate that CRANAD-3 would be able to monitor Aβ species loading at the very early stage, at which low molecular weight Aβ species have been suggested as predominant species. To verify this, the inventors imaged 2-month old APP-PS1 mice (n=6) and age matched wild-type mice (n=6) as control group by following the above procedure for 14-month old mice. Indeed, significant differences between the transgenic group and the control group could be observed from the images and semi-quantitative analysis (FIG. 5C, D and FIG. 7) at 60, 120, 240 min (the difference at 480 min wasn't significant). These data pointed to the feasibility of monitoring the loading of low-molecular weight Aβ species at the very early stage by CRANAD-3. Furthermore, the inventors found that the relative signal intensities F(t)/F (pre) of 14-month old transgenic mice were considerably higher than that of 2-month old transgenic mice, while the signal of 14-month and 2-month old controls were similar. By comparing the normalized signals of these two groups of transgenic mice, the inventors observed slower decay of signal in the 14-month old group (FIG. 8). Taken together, this probe demonstrates that compounds described herein have the capability to detect the Aβ loading abnormality at the very early stage and to distinguish between the age groups.

Example 4

Non-Conjugated Small Molecules Förster Resonance Energy Transfer (FRET) and Potential Application for Differentiating Amyloid Beta Species Material and Methods Reagents used for synthesis were purchased from Aldrich and used without further purification. Column chromatography was performed on silica gel (SiliCycle Inc., 60 Å, 40-63 mm) slurry packed into glass columns. Synthetic amyloid-β peptide (1-40) was purchased from rPeptide (Bogart, Ga., 30622) and aggregates for in vitro studies were generated by slow stirring for 3 days in PBS buffer at room temperature. Curcumin, CRANAD-2, and CRANAD-5 were dissolved in DMSO to make stock solutions at 25.0 μM concentration. $^1$H and $^{13}$C NMR spectra were recorded at 500 MHz and 125 MHz respectively, and were reported in ppm downfield from tetramethylsilane. Fluorescence studies were carried out using a F-4500 Fluorescence Spectrophotometer. Mass spectra were obtained at the Harvard University, Department of Chemistry Instrumentation Facility. In vitro phantom imaging was recorded using the Kodak Imaging Station 2000MM.

Synthesis of CRANAD-2 and CRANAD-5

CRANAD-2: The synthesis was performed according to the inventors' previously reported procedure. (Ran et al. *J. Am. Chem. Soc.* 2009, 131, 15257-61).

CRANAD-5: The synthesis followed the reported procedure with some modifications. (Venkateswarlu, et al. *Bioorg. Med. Chem.* 2005, 13(23): 6374-6380). Boric oxide (700.0 mg, 10.0 mmol) was dissolved in DMF (10.0 mL) at 120° C. Ensuring that most of the boric oxide dissolved was crucial for obtaining a high yield. Acetylacetone (1.1 mL, 10.0 mmol) was added to this solution, followed by tributyl borate (5.4 mL, 20.0 mmol) at 110° C. The solution was stirred for 5 min. 4-N,N'-dimethylamino-benzaldehyde (3.1 g, 20.0 mmol) was added to the above borate complex and stirred for 5 min. A mixture of 1,2,3,4-tetrahydroquinoline (0.2 mL) and acetic acid (0.4 mL) in DMF (4.0 mL) was added to the reaction mixture and heated to 120° C. for 2 h. After cooling to room temperature, the reaction mixture was poured into ice-water (500 mL), and a reddish precipitate was collected. The precipitate was further purified by silica gel column using ethyl acetate/hexanes (50:50) as eluent to give a reddish powder of CRANAD-5 (1.8 g, 52.7%). $^1$H NMR (CDCl$_3$) δ (ppm) 3.03 (s, 6H), 5.73 (s, 1H), 6.42 (d, 2H, J=16.0 Hz), 6.68 (d, 4H, J=10.0 Hz), 7.45 (d, 4H, J=10.0 Hz), 7.60 (d, 2H, J=16.0 Hz); $^{13}$C NMR (CDCl$_3$) δ (ppm) 40.4, 101.1, 112.1, 119.4, 123.3, 130.0, 140.8, 151.8, 183.6. The spectra were consistent with the reported value. (Venkateswarlu, et al.).

Aβ40 Aggregates Preparation

Figure 9:
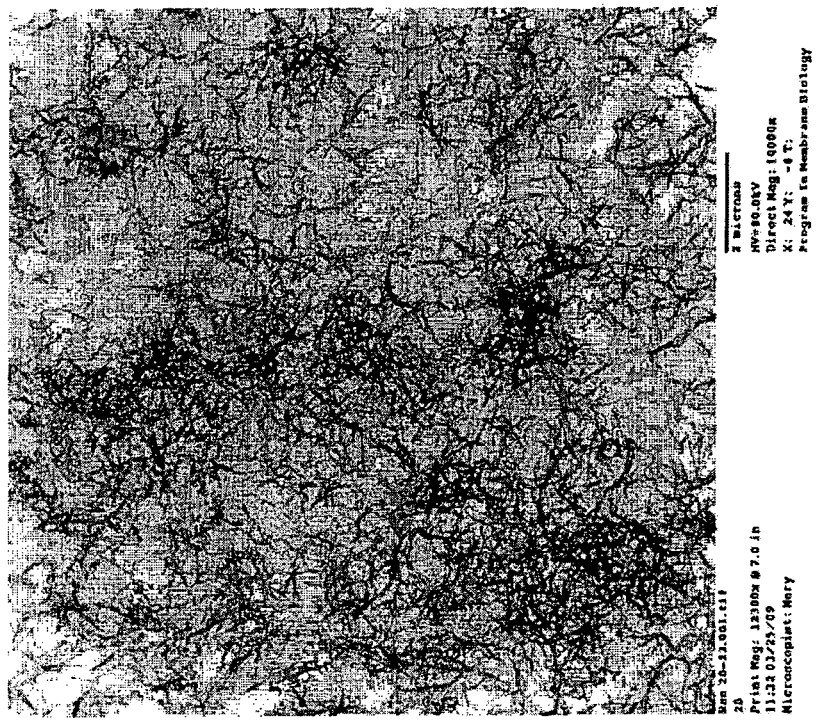
FIG. 9 depicts a transmission electron microscopy image of the Aβ40 aggregates.

Aβ40 peptide (1.0 mg) powder was suspended in 1% ammonia hydroxyl solution (1.0 mL), and 0.1 mL of the resulting solution was diluted tenfold with PBS buffer (pH 7.4) and stirred at room temperature for 3 days. TEM imaging was recorded on JEOL 1011 electron microscope. 10 μL of the Aβ40 peptide solution was mounted on a formava-coated copper grid for 5 minutes, and the grid was dried from the edge of the grid with filter paper. Then 10 ul of 2% aqueous phosphotungstic acid (pH adjusted to 7.3 using 1N NaOH) was dropped onto the grid immediately, and was left on the grid for 30 seconds. The grid was dried off with filter paper and was placed directly into grid box and allowed to air-dry for several hours before observation. The imaging (FIG. 9), which was taken at 80.0 kv with direct magnification of 10,000, confirmed that aggregates were formed. This solution was kept at 4° C. for storage.

Binding Constant Measurements

Various amounts of CRANAD-5 were added to PBS solutions (1.0 mL) of Aβ40 aggregates (2.5 μM, calculation based on Aβ40 peptide concentration) to achieve final CRANAD-5 concentrations of 5.0, 10.0, 20.0, 40.0, 100.0, 200.0 nM. The fluorescence intensities at 610 nm of each solution were recorded (Ex: 520 nm). The dissociation constant ($K_d$) binding curve was generated using Prism 5.0 software with non-linear one-site binding regression to give $K_d$=10.5±2.5 nM.

Spectral Overlap Measurements

Figure 10:
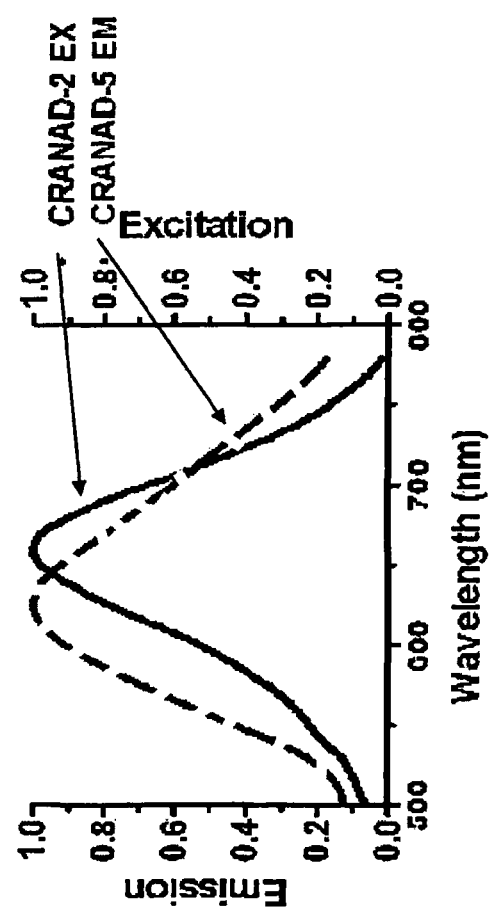
FIG. 10 illustrates the spectral overlap of the emission of CRANAD-5 and the excitation of CRANAD-2.
Figure 11:
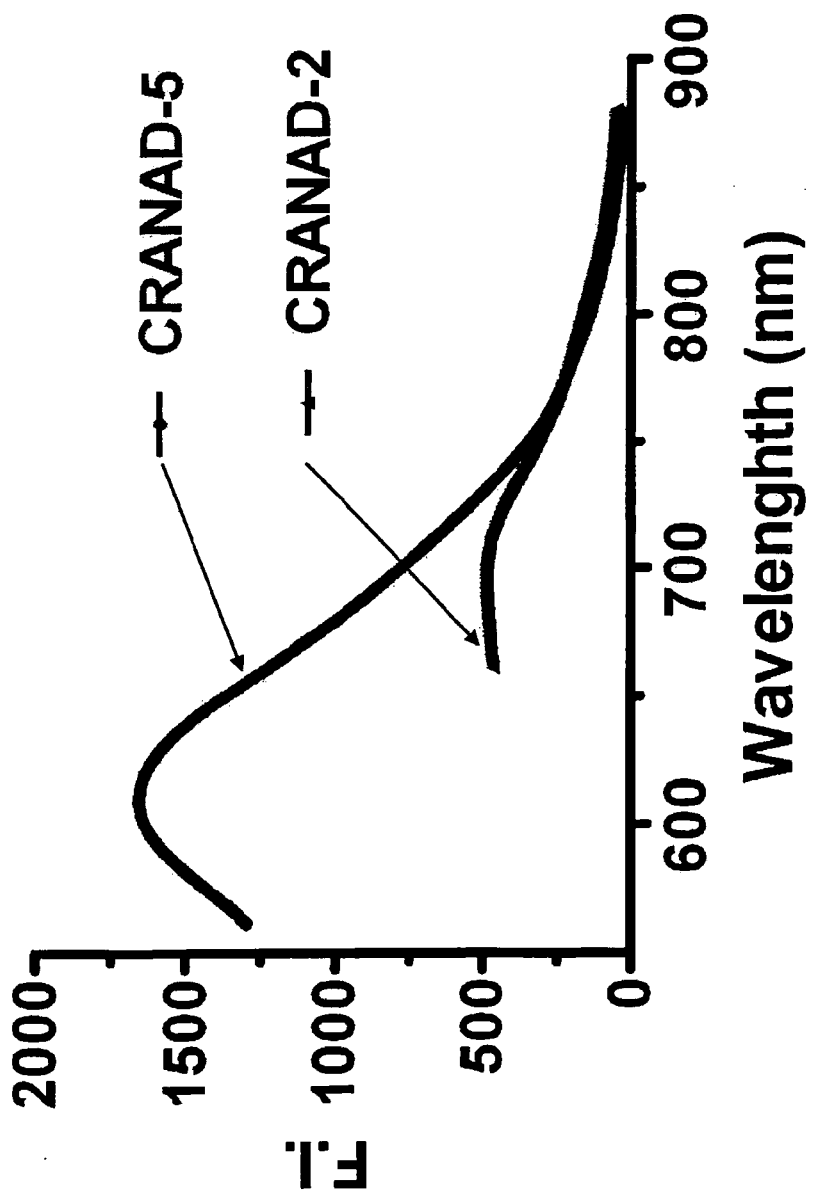
FIG. 11 illustrates the spectral overlay of the emission spectrum of CRANAD-2/CRANAD-5 with maximum excitation.

A solution of curcumin (0.5 μM) and Aβ40 aggregates (1.0 μM) in PBS (1.0 mL) was subjected to emission spectrum recording (Ex: 470 nm, Excitation (Ex) slit=10 nm, and Emission (Em) slit=10 nm), and the spectrum was normalized to the highest reading of 1.0. For the excitation spectrum of CRANAD-2, a solution of CRANAD-2 (0.5 μM) and Aβ40 aggregates (1.0 μM) in PBS (1.0 mL) was used (Em: 800 nm, Ex slit=10 nm, and Em slit=10 nm) and the recorded spectrum was normalized to the highest reading of 1.0. The final spectral overlap was generated using Prism 5.0 software. (FIGS. 10-11).

Figure 12:
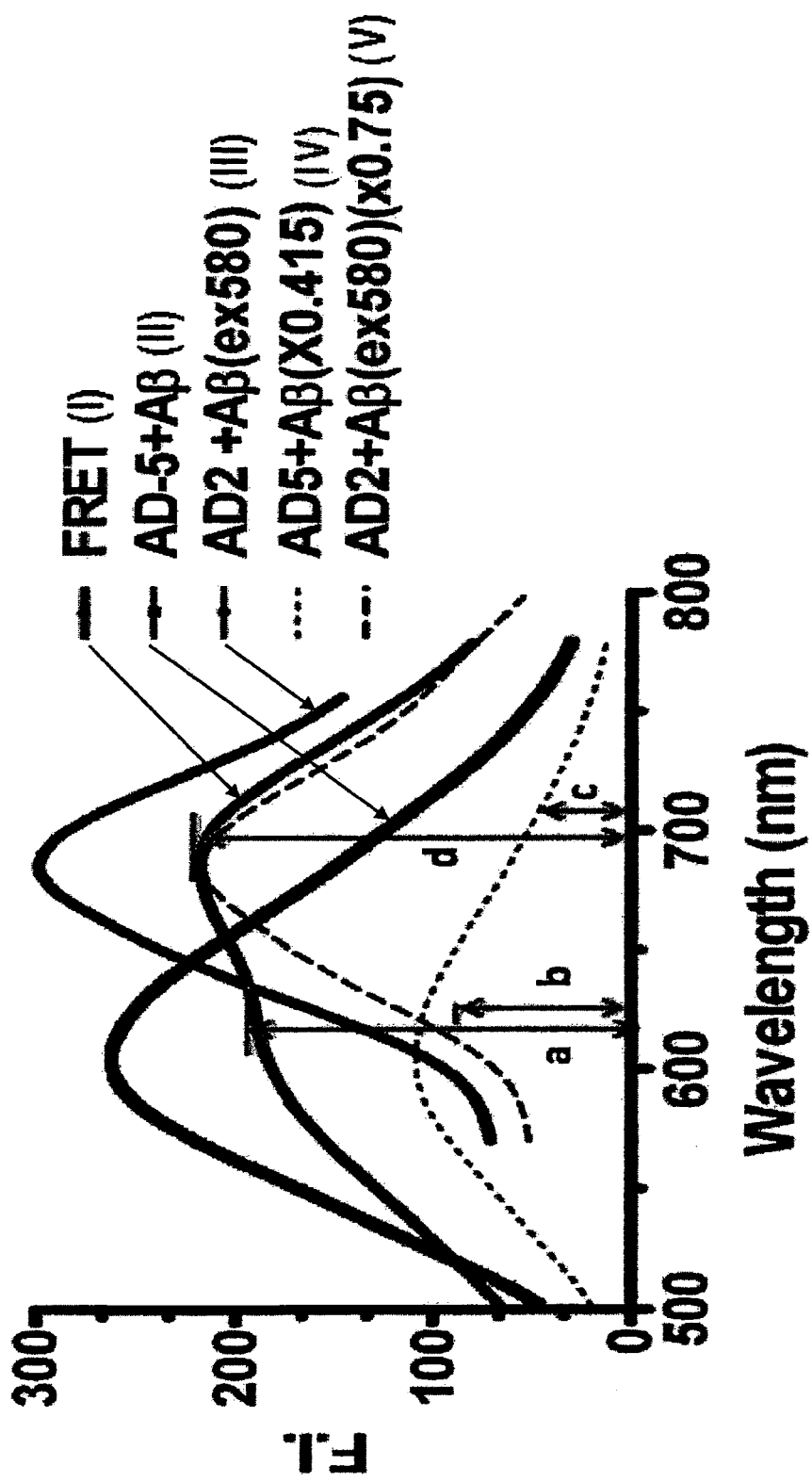
FIG. 12 illustrates the approximate estimation of the actual FRET signal. The (I) line is the measured FRET spectrum; the (II) line is the measured spectrum for CRANAD-5 with Aβ40 aggregates; the (III) line is the measured spectrum for CRA-NAD-2 with Aβ40 aggregates excited at 580 nm; the long dashed line (IV) is the fitting spectrum for CRANAD-5 with aggregates; and the short dashed line (V) is the fitting ideal FRET spectrum without contamination from non-FRET signal of CRANAD-5. Signal contribution estimation: the FRET spectrum (line I) is actually a sum emission spectrum of the actual FRET spectrum (V) without contamination from CRANAD-5 with non-FRETed Aβ40 and the spectrum of CRANAD-5 with non-FRETed Aβ40 (IV). Therefore the measured FI(610 nm(I))=FI(FRET@610 nm(V))+FI(CRA-NAD-5@610 nm(IV)), thus FI(CRANAD-5@610 nm(IV))=FI(610 nm(I))−FI(FRET@610 nm(V))=a−b=84.5; thus actual FI(FRET@700 nM)=FI(700 nm(I))−FI(CRA-NAD-5@700 nm(IV))=d−c=201.2−44.8=156.4.
Figure 13:
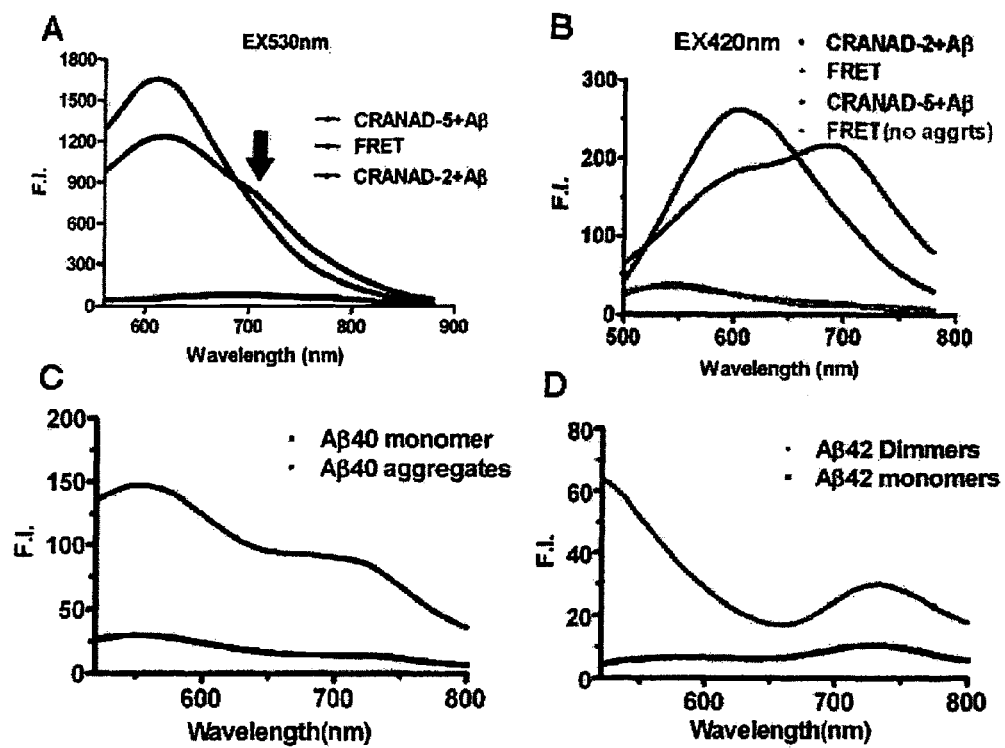
FIG. 13 shows (A) The fluorescence spectra of CRA-NAD-5 with Aβ40 aggregates and FRET spectra of CRA-NAD-5/-2 with Aβ40 aggregates at 530 nm excitation (large arrow: the shroud peak at 710 nm); (B) Spectra overlay (Ex=420 nm) of solution (a) (CRANAD-2+Aβ), solution (b) (FRET), solution (c) (CRANAD-5+Aβ) and solution (d) (FRET (no aggregates); (C) Spectra overlay of Aβ40 aggregates and Aβ40 monomers; (D) Spectra overlay of Aβ42 dimers and Aβ42 monomers.

In Vitro FRET (FIG. 12 and FIG. 13)

A solution of Aβ40 aggregates (1.4 μM) was mixed with 0.5 μM of CRANAD-5 and 0.5 μM of CRANAD-2 (a), and the FRET spectrum was measured after 1 minute incubation (Ex: 420 nm, Ex slit=10 nm, and Em slit=10 nm). Controls included a solution of 0.5 μM CRANAD-5 with Aβ40 aggregates (1.0 μM) (b); a solution of 0.5 μM CRANAD-2 with Aβ40 aggregates (1.0 μM) (c); and a solution of 0.5 μM CRANAD-5 and 0.5 μM CRANAD-2 without aggregates (d).

A similar procedure was used for recording the FRET spectrum of the curcumin/CRANAD-2 pair (Ex: 470 nm, Ex slit=10 nm, and Em slit=10 nm). For excitation spectra recording, Em=700 nm was used, and the Em/Ex slits were 10 nm.

Standard Curve of thioT

Fluorescence spectra of thioT (250 nM) with 50, 100, 150, 200, 250, 300, 400, 500, 750, and 1000 nM Aβ40 aggregates were recorded. The standard curve was plot as Aβ40 aggregates conc. vs FI @510 nm, and fit with linear regression.

Standard Curve of RET

Fluorescence spectra of CRANAD-5/-2 FRET pair (250 nM for both compounds) with 50, 100, 150, 250 nM Aβ40 aggregates were recorded. The standard curve was plot as Aβ40 aggregates conc. vs FI @700 nm, and fit with linear regression.

Example 5

Biodistribution of F-18 Curcuminoid in Mice

Methods

Radiofluorination of the curcuminoid N-2-ethane mesylate was done in a sealed vial containing dry $K^{18}F$/Kryptofix in DMSO for 5 min at 120° C. Once cooled, the mixture was diluted with water and was passed through a C-18 SepPak. Polar materials were eluted with water and F-18 curcuminoid with methylene chloride. The F-18 curcuminoid was purified by HPLC (normal phase). Biodistribution was performed in normal mice at 5, 30 and 60 min after intravenously injecting the F-18 probe in 10% DMSO, 10% Cremophor, and 80% PBS.

Results

Figure 14:
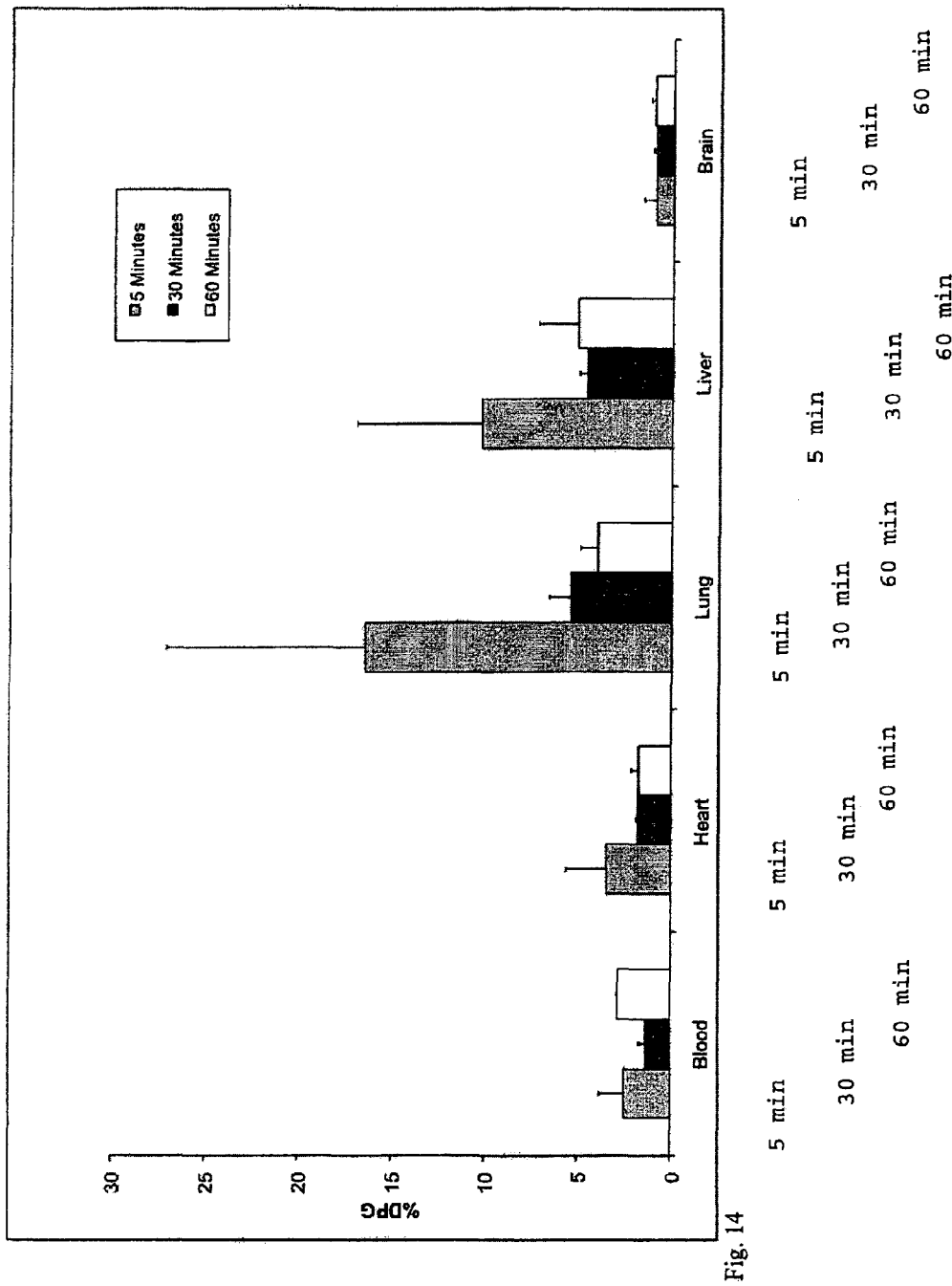
FIG. 14 provides the biodistribution of F-18 curcuminoid in mice.

The [18F]fluoroethylamino curcuminoid can quickly be prepared by this method although dimerization under basic conditions remains a concern. Referring now to FIG. 14, biodistribution showed brain accumulation (DPG): 0.94%, 0.94% and 1.0% at 5, 30, and 60 min, respectively.

Conclusion

The bis-dialkylamino group enhanced brain uptake and stability for this class of compounds. Although washout was not observed at 60 min, this may be due to the control-releasing effect of the injection formulation (Cremophor can form micelles), strong normal brain tissue binding, or both.

Example 6

Imaging of Amyloid Beta Species by Using Spectral Unmixing with a "Smart" Fluorescence Probe Quantifying the concentration of bound fluorescent probe in vivo involves the evaluation of probe signal after a finite wash-out period of free, unbound probe. This process is complicated by the tendency for partially-bound probe to wash away with free probe, leading to an underestimation of bound probe and target quantities. The inventors investigated a method for the real-time assessment of target concentration in vivo using a combination of a commercial spectral unmixing technique and a "smart" fluorescent probe for Aβ species, CRANAD-3.

Figure 15:
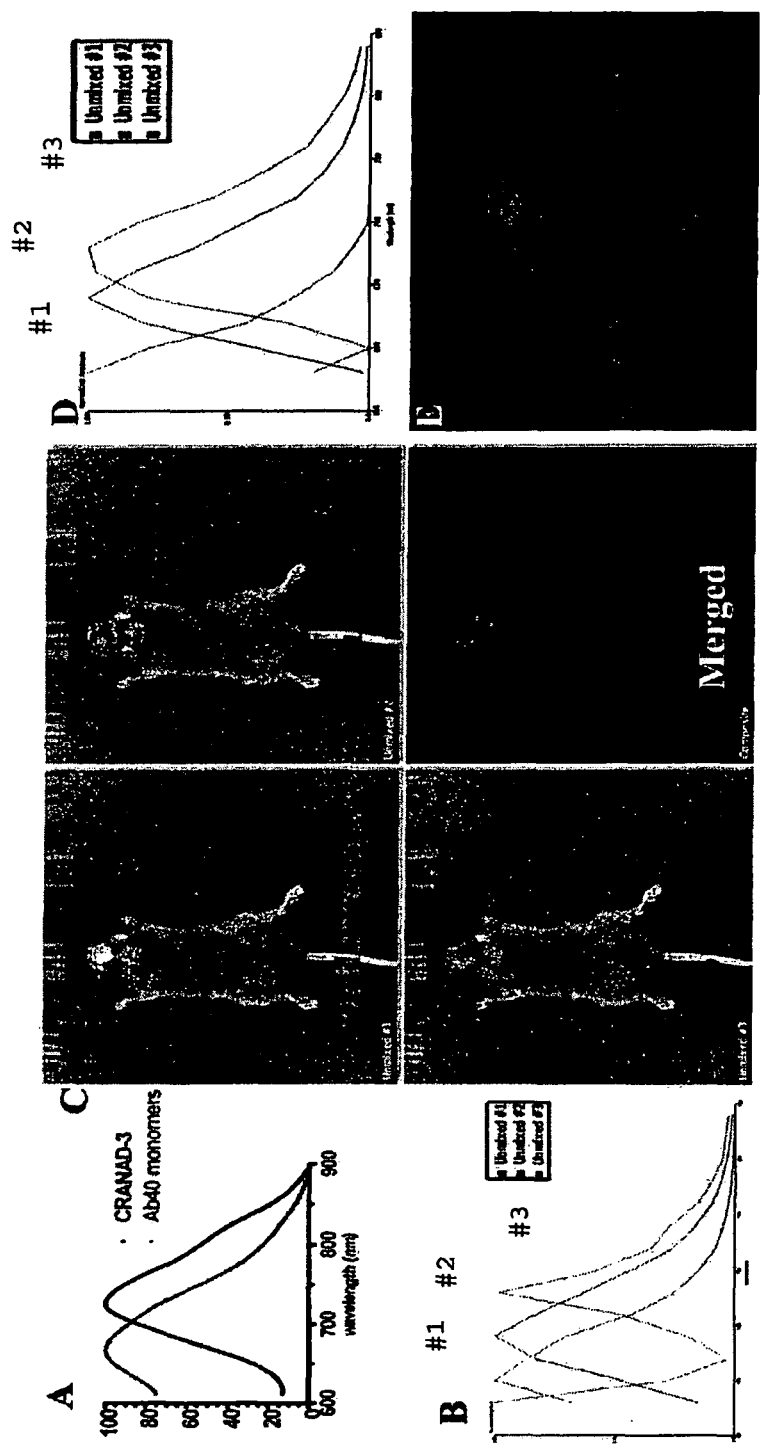
FIG. 15 provides a comparison of bound versus unbound "smart" fluorescence probes in mice.

With this approach the inventors were able differentiate bound from unbound probes in phantoms, in vitro tissues, in vivo transgenic mice and ex vivo brains. In phantom studies the fluorescence intensity of the unmixed bound signal is tightly correlated with the concentration of Aβ and not with the amount of probe added. Tissue staining of transgenic APP/PS1 mouse brain slices revealed that bound CRA-NAD-3 specifically distributed across cortical regions, while unbound CRANAD-3 was randomly deposited throughout the whole tissue. Remarkably, the unmixing imaging results from a 24-month old APP/PS1 mouse showed that the signals of bound CRANAD-3 were unchanged for different injection dosages, a finding that is consistent with the phantom results. In addition, ex vivo unmixing imaging clearly showed that bound probe was primarily located in the cortex while unbound probe was diffusely present in blood vessels, across the whole brain and in the heart (FIG. 15). This indicates that this method will be a useful tool for more reliable detection and monitoring of Aβ species in vivo. To the best of the inventors' knowledge, this is the first demonstration that a real-time assessment of a target concentration is feasible in vivo.

Example 7

In Vitro and In Vivo Testing of Curcumin Analogue as a "Turn-On" Fluorescent Probe for Soluble and Insoluble Amyloid Beta Species One of the major hurdles in the diagnosis of presymptomatic Alzheimer's disease (AD) is the lack of imaging probes capable of detecting early stage biomarkers. Aβ species, which include soluble monomers, dimers, oligomers, and insoluble fibrils and plaques, are widely believed to be important biomarkers for AD. Most of advances in the imaging of AD lesions have focused on the detection of insoluble fibrils and plaques, species present in the symptomatic stage. The inventors' approach focused on developing imaging probes for the detection of soluble Aβ species, the likely early stage biomarkers, and may enable earlier AD detection.

The inventors report that the curcumin derivative, CRA-NAD-3, is able to detect a variety of Aβ species, ranging from insoluble plaques to soluble monomers and even the core fragment (KLVFF) of Aβ40/42. The inventors also show that amino acid K16 of the Aβ peptide is the hot spot for CRA-NAD-3 binding, and the diketone moiety of curcumin and its derivatives is crucial for the interaction. Two-photon imaging results demonstrate that CRANAD-3 is specific to Aβ plaques and able to detect cerebral amyloid angiopathy (CAA) in vivo. Remarkably, in vivo near-infrared imaging (NIR) shows that CRANAD-3 is capable of differentiating between transgenic AD mice and wild-type. Furthermore, CRANAD-3 detects Aβ species in young animals at the early stages of the disease.

These data show the potential for CRANAD-3 to monitor the full course of amyloidosis in AD. This indicates that CRANAD-3, along with its analogues modified to include $^{18}F$ or $^{11}C$, will be valuable tools for early, presymptomatic diagnosis of AD and the assessment of AD therapies.

Other embodiments and uses of the invention will be apparent to those skilled in the art from consideration from the specification and practice of the invention disclosed herein. All references cited herein for any reason, including all journal citations and U.S./foreign patents and patent applications, are specifically and entirely incorporated herein by reference. It is understood that the invention is not confined to the specific reagents, formulations, reaction conditions, etc., herein illustrated and described, but embraces such modified forms thereof as come within the scope of the following claims.

What is claimed is:

1. A method for detecting soluble amyloid beta in a sample, comprising:
   (a) contacting a sample comprising soluble amyloid beta with a compound having the formula $Ar^1$-L-$Ar^2$, wherein
   L is a divalent linking group comprising an alkenylene having 5 to 15 backbone carbon atoms, wherein at least two of the backbone carbon atoms form part of a difluoroboronate ring, and $Ar^1$ and $Ar^2$ are each independently alkyl amine-substituted phenyl or pyridyl groups;
   wherein said compound binds soluble amyloid beta in the sample;
   (b) illuminating said compound bound to the soluble amyloid beta with near infrared light of a wavelength absorbable by said compound; and (c) detecting fluorescence emitted by the compound wherein said fluorescence corresponds to the soluble amyloid beta contained in said sample.

2. The method according to claim 1, wherein the presence, absence or level of said compound's fluorescence in the sample is indicative of Alzheimer's disease.

3. The method according to claim 1, wherein L is

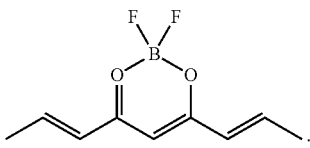

4. The method according to claim 3, wherein Ar$^1$ and Ar$^2$ are independently selected from

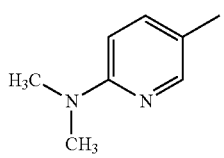 or 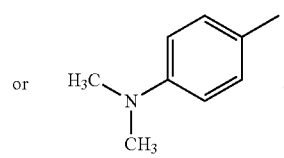

5. The method according to claim 4, wherein said compound has the structure:

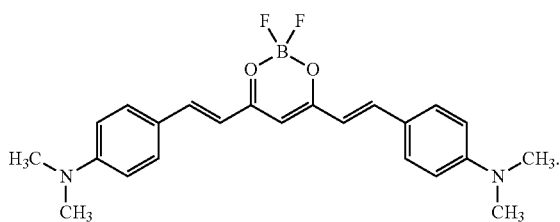

6. The method according to claim 1, wherein Ar$^1$ and Ar$^2$ are independently selected from

 or 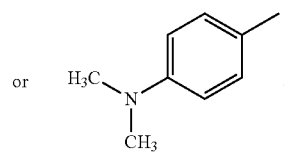

7. An in vivo optical imaging method for soluble amyloid beta detection in a subject, comprising:
(a) administering to a subject a compound having the formula Ar$^1$-L-Ar$^2$, wherein
L is a divalent linking group comprising an alkenylene having 5 to 15 backbone carbon atoms, wherein at least two of the backbone carbon atoms form part of a difluoroboronate ring, and Ar$^1$ and Ar$^2$ are each independently alkyl amine-substituted phenyl or pyridyl groups;
wherein said compound binds soluble amyloid beta contained in the subject;
(b) illuminating said compound bound to the soluble amyloid beta with near infrared light of a wavelength absorbable by said compound; and
(c) detecting fluorescence emitted by the compound wherein said fluorescence corresponds to the soluble amyloid beta contained in said subject.

8. The method according to claim 7, wherein the presence, absence or level of said compound's fluorescence in the subject is indicative of Alzheimer's disease.

9. The method according to claim 7, wherein said compound has the structure:

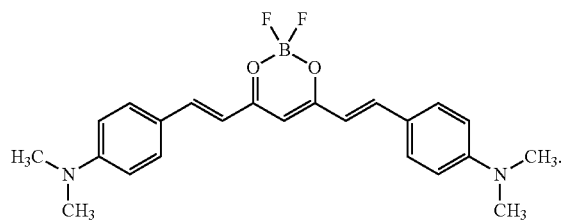

10. A method for providing an image of soluble amyloid beta contained within a subject by positron emission tomography (PET) scan, comprising:
(a) administering to a subject a $^{11}$C or $^{18}$F labeled derivative of a compound having the formula Ar$^1$-L-Ar$^2$, wherein
L is a divalent linking group comprising an alkenylene having 5 to 15 backbone carbon atoms, wherein at least two of the backbone carbon atoms form part of a difluoroboronate ring, and Ar$^1$ and Ar$^2$ are each independently alkyl amine-substituted phenyl or pyridyl groups;
wherein said compound binds soluble amyloid beta contained in the subject; and
(b) imaging gamma rays that are emitted due to the compound being bound to the soluble amyloid beta within said subject in order to provide an image of the soluble amyloid beta contained in said subject.

11. The method according to claim 10, wherein the presence, absence or level of said compound's gamma ray emission in the subject is indicative of Alzheimer's disease.

12. The method according to claim 10, wherein said compound has the structure:

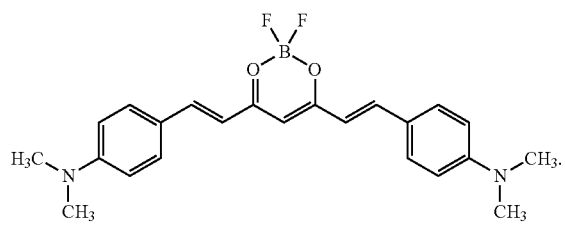

13. A method for providing an image of soluble amyloid beta contained within a subject by magnetic resonance imaging, comprising:
(a) administering to a subject a $^{19}$F labeled derivative of a compound having the formula Ar$^1$-L-Ar$^2$, wherein
L is a divalent linking group comprising an alkenylene having 5 to 15 backbone carbon atoms, wherein at least two of the backbone carbon atoms form part of a difluoroboronate ring, and Ar$^1$ and Ar$^2$ are each independently alkyl amine-substituted phenyl or pyridyl groups;
wherein said compound binds soluble amyloid beta contained in the subject; and
(b) imaging the subject in order to obtain a magnetic resonance image of the compound bound to the soluble amyloid beta and contained within the subject.

14. The method according to claim 13, wherein the presence, absence or level of said compound's magnetic resonance emission in the subject is indicative of Alzheimer's disease.
15. The method according to claim 13, wherein said compound has the structure:
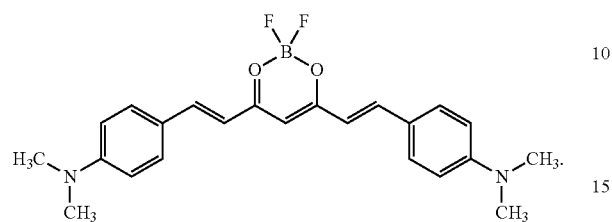
* * * * *